US006908914B1

(12) United States Patent
Boigegrain et al.

(10) Patent No.: US 6,908,914 B1
(45) Date of Patent: Jun. 21, 2005

(54) ANTIPSYCHOTIC CYCLIC N-ARALKYLAMINES

(75) Inventors: Robert Boigegrain, Assas (FR); Martine Bourrie, Saint Gely du Fesc (FR); Pierre Lair, Goyrans (FR); Raymond Paul, Saint Gely du Fesc (FR); Martine Poncelet, Valflaunes (FR); Jean Claude Vernieres, Muret (FR)

(73) Assignee: Sanofi-Synthelabo, Paris (FR)

( * ) Notice: Subject to any disclaimer, the term of this patent is extended or adjusted under 35 U.S.C. 154(b) by 255 days.

(21) Appl. No.: 10/019,205

(22) PCT Filed: Jun. 27, 2000

(86) PCT No.: PCT/FR00/01790

§ 371 (c)(1),
(2), (4) Date: Mar. 12, 2002

(87) PCT Pub. No.: WO01/02380

PCT Pub. Date: Jan. 11, 2001

(30) Foreign Application Priority Data

Jul. 2, 1999 (FR) .............................. 99 08532

(51) Int. Cl.⁷ .................... A61P 25/18; A61K 31/55; C07D 223/00
(52) U.S. Cl. ............... 514/212.01; 514/217.03; 540/484; 540/596; 540/609
(58) Field of Search ............... 514/212.01, 217.03; 540/484, 596, 609

(56) References Cited

U.S. PATENT DOCUMENTS

| 5,231,092 A | 7/1993 | Lavastre et al. ............ 514/212 |
| 5,296,596 A | 3/1994 | Lavastre et al. ............ 540/612 |
| 6,235,791 B1 | 5/2001 | Breliere et al. ............ 514/650 |

FOREIGN PATENT DOCUMENTS

| EP | 0461986 | 12/1991 |
| FR | 2159369 | 6/1973 |
| WO | WO 89/12443 | 12/1989 |
| WO | WO 95/30659 | 11/1995 |
| WO | WO 98/04251 | 2/1998 |

OTHER PUBLICATIONS

Chemical Abstract No. 118:2375 (1993).
Chemical Abstract No. 119:130911 (1983).
Chemical Abstract No. 83:97373 (1975).
Zhang, M. Q. et al., J. Pharm. Pharmacol., vol. 45, No. 1, pp. 63–66 (1993).
Zhang, M. Q. et al., Chirality, US, vol. 6, No. 8, pp. 631–641 (1994).
Reitz, Allen B. et al., J. Med.Chem., vol. 41, No. 12, pp. 1997–2009 (1998).
Derwent Patent Abstract No. 197322 (2001).

*Primary Examiner*—Brenda Coleman
(74) *Attorney, Agent, or Firm*—Balaram Gupta

(57) ABSTRACT

The invention relates to benzene derivatives, to pharmaceutical compositions containing them, to processes for preparing them, and to the method of use thereof in the treatment of psychotic disorders.

27 Claims, No Drawings

ANTIPSYCHOTIC CYCLIC N-ARALKYLAMINES

The present invention relates to benzene derivatives comprising a cyclic amine which binds specifically to sigma receptors, in particular to those of the central nervous system, to a process for preparing these compounds and to their use in pharmaceutical compositions and more particularly as antipsychotic agents.

Sigma receptors have been revealed with the aid of several ligands. Firstly, mention may be made of opiate compounds, 6,7-benzomorphans or SKF-10,047, more particularly the chiral compound (+)SKF-10,047 (W. R. Martin et al., J. Pharmacol. Exp. Ther. 1976, 197, 517–532; B. R. Martin et al., J. Pharmacol. Exp. Ther. 1984, 231, 539–544). Among these compounds, the ones most commonly used are (+)N-allylnormetazocin or (+)NANM and (+)pentazocin. A neuroleptic agent, haloperidol, is also a sigma receptor ligand, as are (+)3-(3-hydroxyphenyl)-1-propylpiperidine and (+)3-PPP (B. L. Largent et al., Proc. Nat. Acad. Sci. USA 1984, 81, 4983–4987).

U.S. Pat. No. 4,709,094 describes guanidine derivatives which are very active as sigma receptor-specific ligands, and mention may be made more particularly of di-(o-tolyl) guanidine or DTG. The anatomical distribution of the sigma receptors in the brain has been studied by autoradiography, after labelling of these receptors with DTG according to E. Weber et al., Proc. Nat. Acad. Sci. USA 1986, 83, 8784–8788, as well as with the ligands (+)SKF-10,047 and (+)3-PPP according to B. L. Largent et al., J. Pharmacol. Exp. Ther. USA 1986, 238, 739–748. The autoradiography study made it possible to identify the sigma receptors in the brain clearly and to distinguish them from the other opiate receptors, as well as from the phencyclidine receptors. Sigma receptors are particularly abundant in the central nervous system and are concentrated in the brainstem, the limbic system and the regions involved in regulating the emotions. Sigma receptors are also found in various peripheral tissues. Thus, two sorts of sigma receptor are distinguished. Ligands of type (+)SKF-10,047 bind selectively to the sigma-1 receptors, while other ligands such as DTG, haloperidol or (+)3-PPP exhibit great affinity for both the sigma-1 and sigma-2 receptors.

Patent EP 461 986 describes compounds of formula:

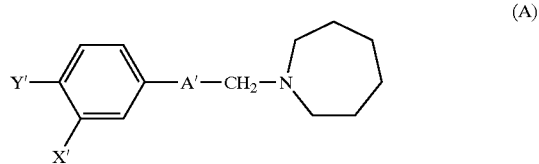

(A)

which bind selectively to sigma receptors and which have antipsychotic activity.

Among this series of compounds, (Z)-1-[3-(3-chloro-4-cyclohexylphenyl)allyl]azepane hydrochloride, of formula:

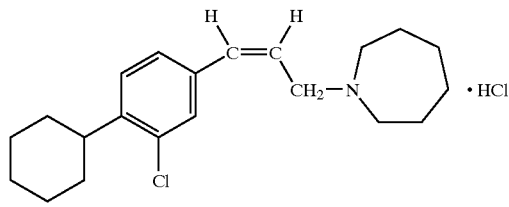

has been studied in particular. Reference may be made, for example, to Neuropharmacology 1993, 32 (6), 605–615 and Eur. J. Pharmacol. 1993, 231 (3), 465–467.

However, the compounds of formula (A) have a specific property which might be considered as a drawback. It is a property which appears during metabolism: dependency on the cytochrome P450 termed CYP 2D6.

In 1957, it was envisaged for the first time that hereditary differences could be responsible for variations in response to medicinal products.

Oxidative metabolism shows large variations between individuals and races. The research carried out in the last 15 years has shown that the variations in the functional expression of the multigenic cytochrome P450 (CYP) family is the cause of these differences. Only a few isoforms of cytochrome P450 among those already characterized in humans have a role in the oxidative metabolism of medicinal products. Reference may be made to Xenobiotica 1986, 16, 367–378. Until now, GYP 1A2, CYP 2A6, CYP 2C9, CYP 2D6, CYP 2C19, CYP 2E1 and CYP 3A4 have been identified on the basis of their clinical importance. Currently, it is estimated that CYP 3A4, CYP 2D6 and CYP 2C9 are responsible by themselves (and to variable degrees) for 90% of the oxidative metabolism of medicinal products. Although the functional expression of these isoforms is regulated and influenced by a good number of environmental and physiological factors, genetic factors have the most pronounced influence, which underlines the important role played by polymorphism in the oxidation of medicinal products. A certain number of these polymorphisms have been studied (particularly those of CYP 2C19 and CYP 2D6). More particularly, the clinical importance of the polymorphism of CYP 2D6 in the 4-hydroxylation of debrisoquine has been demonstrated (Clin. Pharmacol. Ther. 1991, 50, 233–238). The genetic polymorphism of CYP 2D6 is responsible for the problematic metabolism of more than 30 important medicinal products and effects up to 10% of the Caucasian population (slow metabolizers). It has now been shown that this isoform controls the biotransformation of medicinal products such as antiarrythmic agents, β-blockers, antihypertensive agents, antiangina agents, neuroleptic agents and antidepressants. Apart from a few exceptions, these medicinal products are used in psychiatric and cardiovascular medicine for long-term treatment.

The pharmacokinetic consequences are especially of quantitative order: slow-metabolizing individuals have a level of unchanged product which is higher than the others. These quantitative differences have a considerable clinical impact for molecules which have a low therapeutic index.

Genetics thus greatly influences the differences in efficacy and side effects observed from one individual to another. Thus, it is important to determine whether the metabolism of a medicinal product may be modified in the event of a genetic deficiency of an enzyme.

Novel fine benzene derivatives for the sigma receptors, in particular those of the central nervous system, have now been found according to the present invention, which have antipsychotic activity, but have a low rate of metabolization and/or little or no involvement of CYP 2D6 in the oxidative process.

Thus, according to one of its aspects, the present invention relates to the compounds of formula (I):

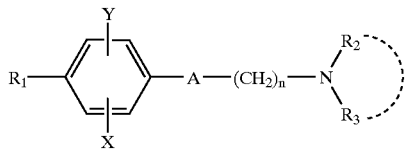

(I)

in which:

A represents a group chosen from the following:

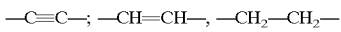

—C≡C—; —CH=CH—, —CH₂—CH₂— n is equal to 1 or 2;

X represents a hydrogen, chlorine or fluorine atom or a methyl or methoxy group;

Y represents a hydrogen atom or a chlorine or fluorine atom;

$R_1$ represents a cyclohexyl group monosubstituted, disubstituted, trisubstituted or tetrasubstituted with a methyl group; a phenyl group monosubstituted or disubstituted with a fluorine or chlorine atom or with a $(C_1–C_3)$alkoxy or trifluoromethyl group; a cycloheptyl, tert-butyl, dicyclopropylmethyl, bicyclo[3.2.1]octanyl, 4-tetrahydropyranyl, 4-tetrahydrothiopyranyl or 1- or 2-adamantyl group; or $R_1$ represents a phenyl group, it being understood that, in this case, X or Y is other than hydrogen; or else $R_1$ represents a cyclohexyl group, it being understood that, in this case, X and Y are other than hydrogen;

$R_2$ and $R_3$ form, with the nitrogen atom to which they are bonded, a 5- to 8-membered amine ring; a morpholinyl group optionally substituted in positions 3 and 5 with a methyl; or a 4-phenyl-1,2,3,6-tetrahydropyridyl group optionally substituted on the phenyl with a halogen or a trifluoromethyl, $(C_1–C_4)$alkyl or $(C_1–C_4)$alkoxy group;

and the addition salts of these compounds with pharmaceutically acceptable acids, as well as the solvates and hydrates thereof.

"Alkyl" is intended to mean a linear or branched, saturated, hydrocarbon-based monovalent radical.

"$(C_1–C_4)$alkyl" is intended to mean an alkyl radical comprising 1 to 4 carbon atoms.

"Alkoxy" is intended to mean an O-alkyl radical.

Among these compounds of formula (I) are preferred those in which:

A represents a group chosen from the following:

—C≡C—; —CH=CH—, —CH₂—CH₂— n is equal to 1;

X represents a hydrogen or chlorine atom or a methyl group;

Y represents a hydrogen or chlorine atom;

$R_1$ represents a cyclohexyl group monosubstituted, disubstituted, trisubstituted or tetrasubstituted with a methyl group; a phenyl group monosubstituted or disubstituted with a fluorine or chlorine atom or with a methoxy or trifluoromethyl group; a tert-butyl or 1- or 2-adamantyl group; or $R_1$ represents a phenyl group, it being understood that, in this case, X and Y are other than hydrogen; or else $R_1$ represents a cyclohexyl group, it being understood that, in this case, X and Y are other than hydrogen;

$R_2$ and $R_3$ form, with the nitrogen atom to which they are bonded, a 6- to 8-membered amine ring;

and the addition salts of these compounds with pharmaceutically acceptable acids, as well as the solvates and hydrates thereof.

Among the latter compounds of formula (I), the compounds of formula:

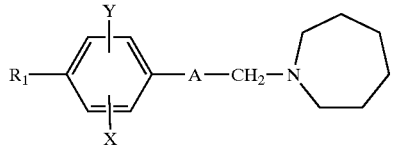

(I.1)

in which:

A represents a group chosen from the following:

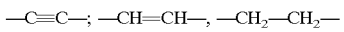

—C≡C—; —CH=CH—, —CH₂—CH₂—

X represents a hydrogen or chlorine atom;

Y represents a hydrogen atom or a chlorine atom;

$R_1$ represents a cyclohexyl monosubstituted, disubstituted, trisubstituted or tetrasubstituted with a methyl group; a phenyl group mono- or disubstituted with a fluorine or chlorine atom or a methoxy group; a tert-butyl or 1- or 2-adamantyl group;

$R_1$ represents a cyclohexyl or phenyl group, it being understood that, in this case, X and Y are other than hydrogen;

and the addition salts of these compounds with pharmaceutically acceptable acids, as well as the solvates and hydrates thereof, are particularly preferred.

Among the latter compounds (I.1), the compounds in which A represents the —CH=CH— group, in particular of configuration (Z), are preferred.

Also preferred are the compounds of formula (I.1) in which X represents a chlorine atom, preferably in position 3 of the phenyl, and Y represents a hydrogen atom, and the addition salts of these compounds with pharmaceutically acceptable acids, as well as the solvates and hydrates thereof.

Particularly preferred are the compounds of formula (I.1) in which $R_1$ represents a phenyl group monosubstituted or disubstituted with a fluorine or chlorine atom or a methoxy group, and the addition salts of these compounds with pharmaceutically acceptable acids, as well as the solvates and hydrates thereof.

The following compounds are particularly preferred:

1-[(Z)-3-(2-chloro-3'-fluorobiphenyl-4-yl)propen-2-yl] azepane;

1-[(Z)-3-(2-chloro-3'-5'-difluorobiphenyl-4-yl)propen-2-yl]azepane;

and in particular 1-[(Z)-3-(2-chloro-3'-methoxybiphenyl-4-yl)propen-2-yl]azepane;

as well as the salts thereof with pharmaceutically acceptable acids, the solvates and hydrates thereof.

The salts of the compounds according to the invention are prepared according to techniques well known to persons skilled in the art.

The salts of the compounds of formula (I) according to the present invention comprise those with inorganic or organic acids which allow a separation or a suitable crystallization of the compounds of formula (I), as well as of the pharmaceutically acceptable salts. Suitable acids which may be mentioned are: picric acid, oxalic acid or an optically active acid, for example a tartaric acid, a dibenzoyltartaric acid, a mandelic acid or a camphorsulphonic acid, and those which form physiologically acceptable salts, such as the hydrochloride, hydrobromide, sulphate, hydrogensulphate, dihydrogenphosphate, maleate, fumarate, 2-naphtalenesulphonate, or para-toluenesulphonate. The hydrochlorides are most particularly preferred among the salts of the compounds of formula (I).

When a compound according to the invention has one or more asymetric carbons, the optical isomers of this compound form an integral part of the invention.

When a compound according to the invention exhibits a stereoisomerism, for example of axial-equatorial or Z-E type, the invention comprises all the stereoisomers of this compound.

The present invention comprises the compounds of formula (I) in the form of pure isomers, but also in the form of a mixture of isomers in any proportion. The compounds (I) are isolated in the form of pure isomers by the conventional separation techniques: use may be made, for example, of fractional recrystallizations of a salt of the racemic mixture with an optically active acid or base, the principle of which is well known, or the conventional chromatography techniques on a chiral or nonchiral phase; for example, use may be made of separation on silica gel or $C_{18}$-grafted silica gel, eluting with mixtures such as chlorinated solvents/alcohol.

The compounds of formula (I) above also comprise those in which one or more hydrogen, carbon or halogen atoms, in particular chlorine or fluorine atoms, have been replaced with their radioactive isotope, for example tritium or carbon-14. Such labelled compounds are useful in research studies, of metabolism or pharmacokinetics, and in biochemical assays as receptor ligands.

The functional groups possibly present in the molecule of the compounds of formula (I) and in the reaction intermediates can be protected, either in permanent form or in temporary form, with protecting groups which ensure an unequivocal synthesis of the expected compounds. The protection and deprotection reactions are carried out according to techniques well known to persons skilled in the art. The expression "temporary protecting group for amines, alcohols, phenolthiols or carboxylic acids" is intended to mean protecting groups such as those described in Protective Groups in Organic Synthesis, Greene T. W. and Wuts P. G. M., ed. John Wiley and Sons, 1991 and in Protecting Groups, Kocienski P. J., 1994, Georg Thieme Verlag.

Persons skilled in the art will be capable of selecting the appropriate protecting groups.

The compounds of formula (I) can comprise precursor groups for other functions which are generated subsequently or in one or more steps.

A subject of the present invention is also a method for preparing the compounds of formula (I), characterized in that:

1) when A represents a —C≡C— group:
a) either, if n=1, a Mannich reaction is carried out between the phenylacetylene derivative of formula:

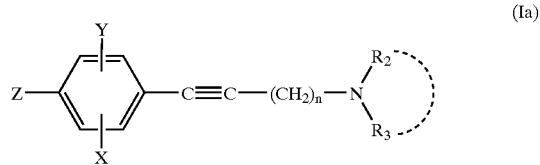

(II)

in which $R_1$, X and Y are as defined for (I), the formaldehyde and the amine (1) $HNR_2R_3$, $R_2$ and $R_3$ being as defined for (I);

b) or a Suzuki coupling is carried out between the compound of formula:

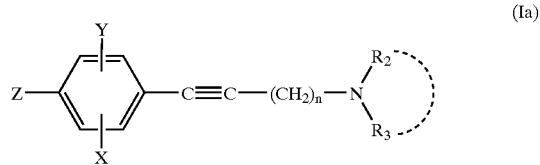

(Ia)

in which X, Y, n, $R_2$ and $R_3$ are as defined for (I) and Z represents a bromine, an iodine or a trifluoromethanesulphonate (OTf) group and a boron derivative (2) of formula $R_1$—$B(OR)_2$ in which R represents a hydrogen atom, an alkyl or aryl group in the presence of a base and a metal catalyst;

c) or, when $R_1$ represents a cyclohexyl group monosubstituted, disubstituted, trisubstituted or tetrasubstituted with a methyl group; a cycloheptyl, 4-tetrahydropyranyl, 4-tetrahydrothiopyranyl or adamantyl group, a coupling is carried out between compound (Ia) in which Z represents an iodine or bromine atom and the ketone (3) corresponding to $R_1$ represented by

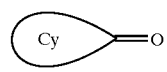

in the presence of a base, to give the intermediate compound of formula:

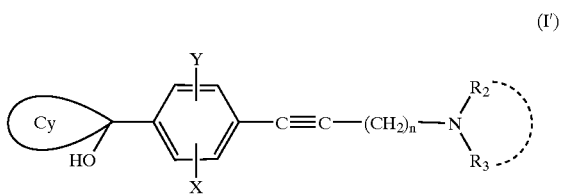

(I')

in which X, Y, n, $R_2$ and $R_3$ are as defined for (I); said compound (I') then being reduced under selective conditions;

d) or a coupling reaction is carried out between the amine of formula:

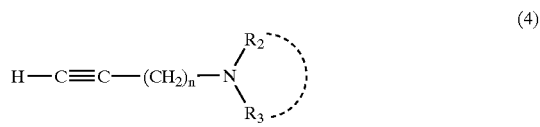

(4)

in which n, $R_2$ and $R_3$ are as defined for (I), and the compound of formula:

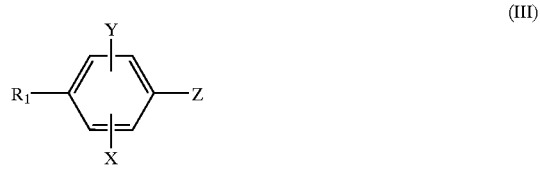

(III)

in which $R_1$, X and Y are as defined for (I) and Z represents a bromine or iodine atom or a trifluoromethylsulphonate (triflate or OTf) group;

2) when A represents a —CH=CH— group, a hydrogenation is carried out, with nascent hydrogen or in the presence of cyclohexene, of compound (l) in which A represents an acetylene group —C≡C—, in order to prepare the ethylenic compound (I) in the form of a mixture of the Z and E isomers, or this hydrogenation is carried out in the presence of a metal catalyst on a support in order to prepare the ethylenic compound (I) in Z form, or alternatively compound (I) in which A represents an acetylene group —C≡C— is reacted with a metal hydride in order to prepare the ethylenic compound (I) in E form;

3) when A represents a —CH$_2$—CH$_2$— group, a hydrogenation is carried out on compound (I) in which A represents a —CH=CH— or —C≡C— group.

Step 1a of the process according to the invention is carried out with heating, preferably at a temperature between 80 and 90° C., in a polar solvent such as 1,2-dimethoxyethane or 1,4-dioxane. To facilitate the condensation reaction, a catalyst can be used, for example a metal salt such as copper II chloride or copper III chloride. In step 1b of the process, the Suzuki coupling is preferably carried out between a compound (Ia) in which Z represents OTf and the boron derivative (2) of formula R$_1$—B(OH)$_2$. The reaction is carried out in the presence of a base, such as alkali metal or alkaline-earth metal hydroxides, alkoxides, phosphates or carbonates, more particularly potassium phosphate or sodium carbonate. The reaction is carried out in the presence of a metal catalyst, for example a copper, tin or, preferably, palladium catalyst, such as tetrakis(triphenylphosphine)palladium optionally with a halide such as lithium chloride acting as co-catalyst. The process is carried out with heating, at a temperature of between 60 and 80° C. in an inert solvent such as toluene or 1,2-dimethoxyethane or preferably in a toluene/aqueous solution two-phase medium optionally with a portion of alcohol such as ethanol.

Suzuki coupling has been studied in many publications such as, for example, Synth. Commun. 1981, 11(7), 513–519 and J. Org. Chem. 1993, 58 (8), 2201–2208. The boronic acids (2) R$_1$—B(OH)$_2$ are commercially available or conventionally synthesized from the corresponding halo, preferably bromo, derivatives R$_1$Br by action for example of trimethylborate in the presence of a base such as tert-butyllithium.

In step 1c, the coupling is preferably carried out on a compound (Ia) in which Z represents a bromine atom, in the presence of a base such as n-butyllithium in an inert solvent, preferably diethyl ether at low temperature, the preferred temperature range being −80 to −70° C. The reduction of (I′) to (I) is carried out under selective conditions, for example according to the method described in Tetrahedron, 1995, 51, 11043–11062 by the action of chlorotrimethylsilane and sodium iodide in a mixture of acetonitrile/chlorinated solvent such as dichloromethane, followed by a treatment with acetic acid in the presence of zinc, or alternatively by the action of hydriodic acid or by ionic hydrogenation by the action of sodium tetraborohydride in triflic acid.

In step 1d of the process, the coupling is carried out in the presence of a palladium catalyst, one or more tertiary amines and optionally lithium chloride. A compound (III) in which Z represents a triflate will preferably be used, and the process will be carried out in the presence of a palladium catalyst such as tetrakis(triphenylphosphine)palladium or dichlorodi(triphenylphosphine)palladium and optionally a co-catalyst such as copper iodide. When Z represents a triflate, lithium chloride will also be used. This coupling is preferably carried out in the presence of triethylamine and pyridine at the reflux point of the reaction mixture. For this type of coupling, known as Sonogashira coupling, reference may be made to J. Org. Chem. 1993, 58, 7368–7376 and 1998, 63, 1109–1118; Syn. Lett. 1995, 1115–1116 and Synthesis, 1987, 981.

To prepare the compounds (I) in which A represents the group —CH=CH— in Z form, the hydrogenation is generally carried out in the presence of cyclohexene and a metal catalyst on a support, such as palladium on barium sulphate or calcium carbonate or Raney nickel or, preferably, the Lindlar catalyst, in a solvent which is inert for the reaction, such as petroleum ether or an alcoholic solvent. To prepare the compounds (I) in E form, the metal hydride preferably used is diisobutylammonium hydride (DIBALH) in an inert solvent such as toluene.

To prepare the compounds (I) in which A represents a —CH$_2$—CH$_2$— group, the hydrogenation is generally carried out in an alcohol, for example ethanol, in the presence of a catalyst such as platinum oxide or, preferably, palladium on charcoal. For the techniques for reducing the alkenes and alkynes used above, reference may be made to "Catalytic Hydrogenation. Techniques and Applications in Organic Chemistry", Robert L. Augustine, 1965, Marcel Dekker, Inc. New York.

The general process for preparing the compounds (I) in which A represents an acetylene group —C≡C— is described in Scheme 1 below:

SCHEME 1

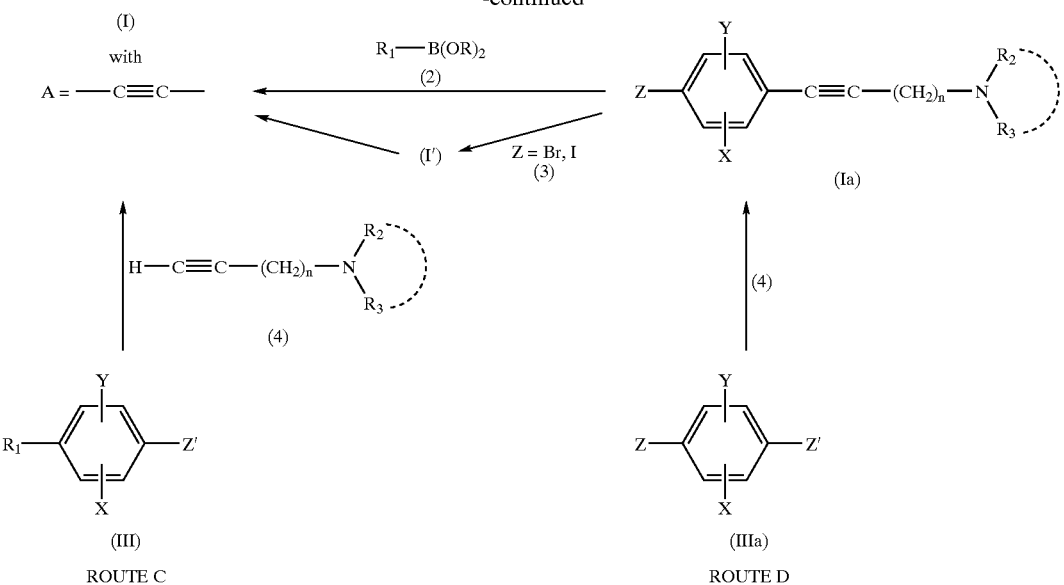

ROUTE C      ROUTE D

In Scheme 1, A=—C≡C—, and X, Y, n, $R_1$, $R_2$ and $R_3$ are as defined for (I), R represents a hydrogen atom or an alkyl or aryl group, Z represents a bromine or iodine atom or a triflate and Z' represents a triflate when Z represents a bromine or iodine, or else Z' represents a bromine or iodine atom. The importance of the nature of the substituents Z and Z' in the coupling reaction labelled ROUTE D will be detailed hereinbelow.

Compound (II) is obtained by treatment in basic medium of the chloroacrolein of formula:

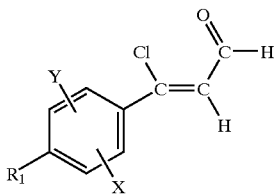

(IV)

in which X, Y and $R_1$ are as defined for (I), preferably by the action of sodium hydroxide in a solvent such as tetrahydrofuran or, preferably, 1,4-dioxane, at the reflux temperature of the solvent.

The chloroacrolein (IV) is prepared from the acetophenone of formula:

(V)

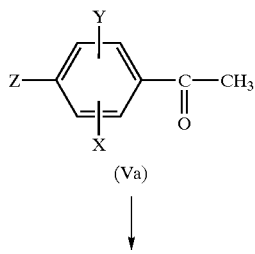

in which X, Y and $R_1$ are as defined for (I), by the action of a Vilsmeier complex. Use is made, for example, of (chloromethylene)dimethylammonium chloride, a commercial Vilsmeier complex, or of a Vilsmeier complex obtained from a disubstituted formamide combined with oxalyl chloride, phosphorus oxychloride or phosgene. The process is generally performed in a chlorinated solvent or an ether at a temperature of between −20° C. and 40° C. A Vilsmeier complex obtained from dimethylformamide and oxalyl chloride in a solvent such as dichloromethane or 1,2-dimethoxyethane at temperatures of between −10° C. and 10° C. is used more particularly.

For this type of reaction, reference may be made, for example, to J. Chem. Soc. (C) 1970, 2484–2488 and Angew. Chem. Internat. Ed. 1963, 2, 98–99.

The acetophenones (V) are known or prepared according to known methods such as those described in Gazz. Chim. Ital. 1949, 79, 453–457 and J. Am. Chem. Soc. 1947, 69, 1651–1652.

Scheme 2 illustrates the methods used to prepare the compounds (V).

SCHEME 2

(Va)

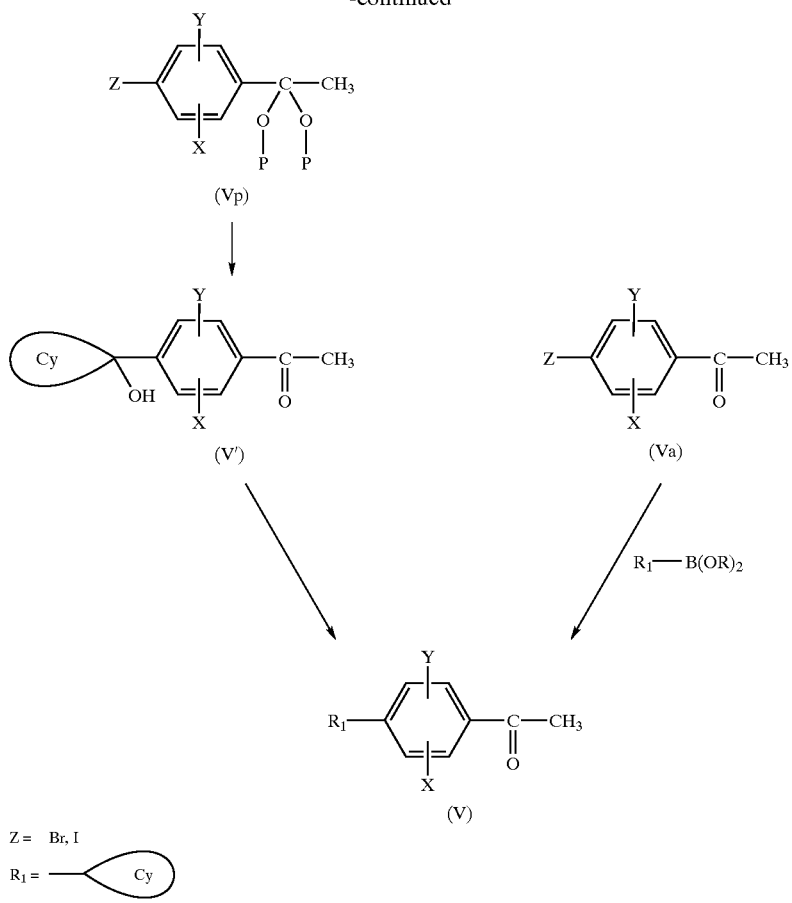

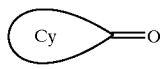

In Scheme 2, X, Y and $R_1$ are as defined for (I), Cy is as defined above for (I'), Z represents a bromine or iodine atom or OTf, R represents a hydrogen atom or an alkyl or aryl group and P represents a protecting group for the ketone function such as a methyl.

The compounds (V) can be obtained directly from the compounds (Va) by the action of the boron compound $R_1$—B(OR)$_2$ (2) as described for the conversion from (Ia) to (I). The ketone function of the compound (Va) can also be protected conventionally, for example by the action of a trialkyl orthoformate in the corresponding alcohol in the presence of an acid such as para-toluenesulphonic acid. The compound (Vp) is thus obtained, which is reacted with the ketone

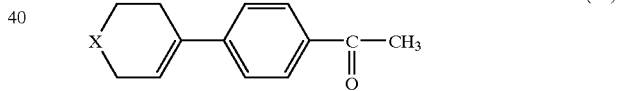

under the conditions described for the conversion from (Ia) to (I'). The ketone function is deprotected by hydrolysis in acidic medium to give the compound (V'). Said compound (V') is then reduced under the mild conditions described for the conversion of (I') to (I).

In certain cases, for example when $R_1$ represents a 4,4-dimethylcyclohexyl or 4-tetrahydropyranyl group, the intermediate compound of formula:

(VI)

in which X=O or —C(CH$_3$)$_2$ may be formed, which will give, after prior protection of the ketone function and hydrogenation, for example in the presence of palladium on charcoal in methanol, followed by deprotection of the ketone function, the desired compound (V).

The compounds (V) in which X and/or Y is other than hydrogen can be obtained from the compounds (V) in which X=Y=H by methods known to persons skilled in the art. For example, when X and/or Y represents a chlorine atom, chlorination of the aromatic nucleus is carried out by the action of gaseous chlorine in the presence of a Lewis acid, preferably aluminium trichloride, in a chlorinated solvent such as dichloromethane, preferably at 0° C.

The compounds (Va) are commercially available or can be prepared according to methods known to persons skilled in the art.

For example, when Z represents a triflate, the compound (Va) can be prepared as shown in SCHEME 3:

SCHEME 3

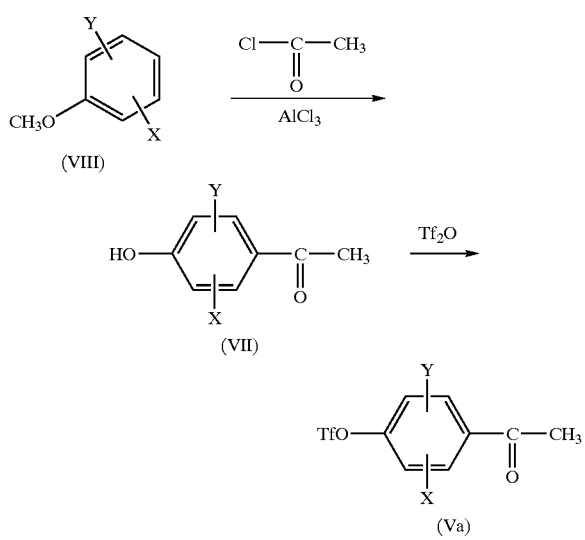
(VIII) → (VII) → (Va)

In Scheme 3, X and Y are as defined for (I). The compounds (VIII) are commercially available or prepared conventionally.

According to another of its aspects, a subject of the present invention is also the compounds of formula (Ia):

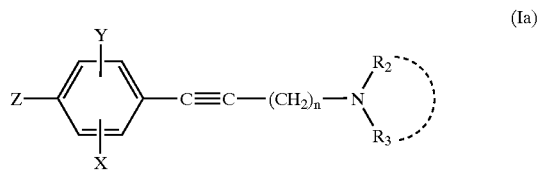
(Ia)

in which X, Y, n, $R_2$ and $R_3$ are as defined for (I) and Z represents a bromine or iodine atom or OTf. These compounds are novel and constitute key intermediates in the synthesis of the compounds (I).

The present invention also relates to a process for preparing the derivatives (Ia) characterized in that:

either, when n=1, a Mannich reaction is carried out between the phenylacetylene derivative of formula:

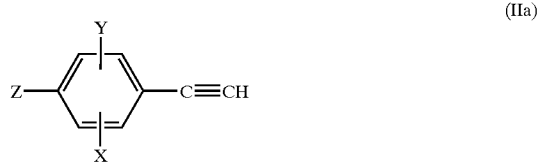
(IIa)

in which X and Y are as defined for (I) and Z represents a bromine or iodine atom or OTf, formaldehyde and the amine (1) $HNR_2R_3$;

or, a coupling reaction is carried out between the amine of formula:

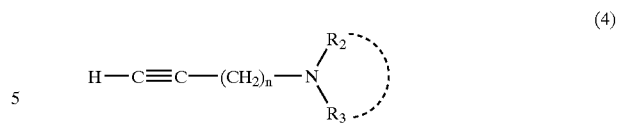
(4)

in which $R_2$, $R_3$ and n are as defined for (I), and the derivative of formula:

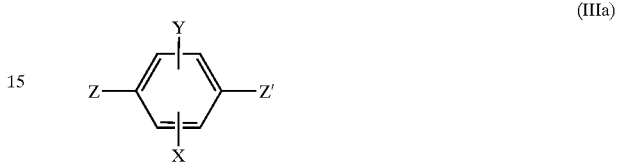
(IIIa)

in which X and Y are as defined for (I), Z represents a bromine or iodine atom or a triflate and Z' represents a bromine or iodine atom if Z represents a triflate, otherwise Z' represents a triflate, in the presence of a palladium catalyst, of one or more tertiary amines and optionally lithium chloride.

The Mannich reaction is carried out under the same conditions as those described for the conversion from (II) to (I).

A Sonogashira reaction described for the coupling of the compounds (III) and (4) is used for the coupling between the compounds (IIIa) and (4). When Z represents a triflate and Z' represents a bromine or iodine atom, the process is performed in the absence of lithium chloride. On the other hand, when Z represents a bromine or iodine atom and Z' represents a triflate, the process is performed in the presence of lithium chloride. The use of lithium chloride makes it possible to direct the coupling reaction.

The propargylamines (4) (in the case where n=1) are prepared conventionally, for example according to Tetrahedron Lett. 1989, 30 (13), 1679–1682 starting with the amine (1) $HNR_2R_3$ and 3-bromopropyne by the action of potassium carbonate in acetonitrile at a temperature of between 50° C. and 80° C.

The compounds (III) in which Z=OTf are conventionally obtained from the corresponding alcohols of formula:

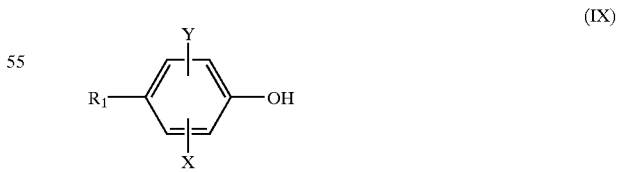
(IX)

in which X, Y and $R_1$ are as defined for (I), by the action of trifluoromethanesulphonic anhydride (triflic anhydride) in pyridine.

The alcohols (IX) are themselves obtained from the compounds of formula:

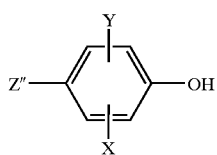

(IXa)

in which Z″ represents a bromine or iodine atom, according to the methods described previously for the conversion from (Ia) to (I) or from (Va) to (V). The compounds (IXa) are commercially available or prepared according to techniques that are well known to persons skilled in the art The compound (IIa) is prepared from the chloroacrolein of formula:

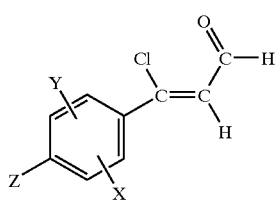

(IVa)

in which X and Y are as defined for (I) and Z represents a bromine or iodine atom or OTf, which is itself obtained from the acetophenone of formula:

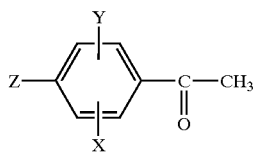

(Va)

in which X, Y and Z are as defined above for (IVa), according to the methods described for the conversion from (IV) to (II) and from (V) to (IV).

The compounds according to the invention have undergone biochemical and pharmacological studies. The compounds of formula (I) and the pharmaceutically acceptable salts, hydrates and solvates thereof bind specifically to the sigma receptors, in particular to those of the central nervous system.

The affinity for the sigma-1 receptors was studied in vitro on guinea pig brain membranes using $^3$H-(+)-pentazocin as ligand, according to De Haven-Hudkins et al., Life Science 1993, 53, 41–48. (+)-Pentazocin binds specifically to the sigma-1 receptors. A guinea pig brain membrane fragment is prepared according to the usual methods. The membrane preparation (0.3 mg of protein/ml) is incubated for 150 minutes at 37° C. in the presence of 0.5 nM [$^3$H]-(+)-pentazocin. The non-specific binding is determined in the presence of 10 μM of (+)-pentazocin. The membranes are then filtered and rinsed 3 times. The filtered material is analysed to determine the fraction of [$^3$H]-pentazocin specifically bound. Under these conditions, the compounds of the invention, examples of which follow, have $IC_{50}$ values of between 0.1 nM and 100 nM.

The capacity of the compounds according to the invention to interact with the sigma-2 receptors was tested in vitro on rat spleen membranes using [$^3$H]-DTG as ligand, according to R. Paul et al., Journal of Neuroimmunology 1994, 52, 183–192. The membrane preparation (1 ml) is incubated with 2 nM [$^3$H]-DTG for 90 minutes at 20° C. The amount of non-specific binding is estimated in the presence of 10 μM of DTG or haloperidol. The membranes are filtered and washed twice, and the filtered material is analysed to determine the amount of [$^3$H]-DTG specifically bound. The compounds according to the invention have a sigma-2 activity of between 1 nM and 500 nM.

The sigma-1 activity was also studied in vivo in mice using the turning model induced with the ligand (+)-3PPP (0.05 μg/ml) according to P. Worms et al., Life Science 1986, 39, 2199–2208. The compounds according to the invention were administered intraperitoneally at doses of 0.25 mg/kg and orally at doses of 1 mg/kg.

The potential antipsychotic activity of the compounds of the invention was studied as follows according to various tests described in Neuropharmacology 1993, 32 (6), 605–615. The compounds according to the invention were studied according to the hyperactivity model induced in mice with amphetamine (intraperitoneally at doses of 2.5 mg/kg) and with cocaine (intraperitoneally at doses of 16 mg/kg). The active avoidance test in rats was also used. These tests showed the antipsyotic activity of the compounds according to the invention, the examples of which are shown below.

The compounds of the invention have also been the subject of electrophysiological studies which show that a similarity exists between the compounds according to the invention and conventional neuroleptic agents, both after single administration and after repeated administration. For some compounds, the results obtained demonstrate great selectivity of the products according to the invention in A10 (ventral tegmental area=VTA) with respect to A9 (substantia nigra), i.e. an increase in the number of spontaneously active dopaminergic neurons uniquely in A10, and not in A9. This property is very interesting, since the A9 structure is highly involved in the extrapyramidal effects obtained with conventional antipsychotic agents (L. A. Chiodo and B. S. Bunney; Catecholamines: Neuropharmacology and Central Nervous System—Theoretical aspects 1984, 369–391).

According to the results observed during these biochemical and behavioural tests, the compounds according to the invention exhibit antipsychotic activity.

The involvement of CYP2D6 can be demonstrated by in vitro metabolism studies on human hepatic microsomal fractions. The most commonly used concept is the inhibition of an enzyme by its specific inhibitor: quinidine used at 20 times its $K_i$, $K_i$ being the absolute value of the inhibition constant of an active principle with respect to an enzyme.

Various models make it possible to demonstrate, in a specific metabolic reaction, the involvement of CYP2D6.

Human hepatic microsomal fractions which contain all of the human hepatic isoforms can be used, which are incubated in the presence of a redox co-factor (NADPH) and in the presence or absence of quinidine at 20 times its $K_i$ with respect to CYP2D6. The decrease in the metabolization observed in the presence of quinidine may be associated with the inhibition of the isoform CYP2D6, which thus proves its possible involvement in the metabolic pathway(s) studied.

Microsomal fractions can also be used which are prepared from transfected cells expressing only one isoform of human cytochrome P-450 (GENTEST Corp.).

Human hepatocytes in primary culture can also be used, which are capable of performing phase I and II metabolic reactions. The incubations are then carried out in time course over 24 hours in the presence or absence of quinidine, which is a potent and specific inhibitor of CYP2D6. Reference may be made to J. Pharm. Exp. Ther. 1996, 277, 321–332.

The compounds according to the invention were particularly studied as follows:

said compound is incubated with human hepatic microsomal fractions, NADPH (redox co-factor), and in the presence or absence of quinidine. The degree of inhibition of the metabolization which is observed in the presence of quinidine reflects the involvement of CYP2D6 in the metabolization of said compound. This approach can be used when the metabolization on hepatic microsomal fractions is of sufficient magnitude (i.e. greater than or equal to 10% of the amount of starting substrate).

When the metabolizaton of said compound on hepatic microsomes is too low to be able to quantify an inhibition with precision, or when further verifications are necessary, further, more extensive studies are carried out on human hepatocytes in primary culture, in time course over 24 hours. The degree of involvement of CYP2D6 in the overall hepatic metabolization is then revealed by the decrease in intrinsic clearance of said compound possibly observed in the presence of quinidine.

The results obtained show that the compounds according to the invention have a low rate of metabolization, and/or that there is a slight involvement of CYP2D6 in the oxidative process.

No sign of toxicity is observed with these compounds at the pharmacologically active doses, and their toxicity is thus compatible with their use as medicinal products.

The compounds of the present invention are thus particularly advantageous and may be advantageously used as medicinal products, in particular as antipsychotic agents, for treating disorders linked to cerebral ischaemia and the positive and negative symptoms of schizophrenia.

The compounds of the invention are also very advantageous for their neuroprotective activity, more particularly with regard to apoptosis.

Moreover, the compounds according to the invention also have an activity in the cardiovascular domain, more particularly for regulating disorders of cardiac rhythm.

A subject of the present invention is thus also pharmaceutical compositions containing an effective dose of a compound according to the invention or of a pharmaceutically acceptable salt, solvate or hydrate of this compound, and suitable excipients.

Said excipients are chosen according to the pharmaceutical form and the desired mode of administration.

In the pharmaceutical compositions of the present invention for oral, sublingual, subcutaneous, intramuscular, intravenous, topical, intratracheal, intranasal, transdermal, rectal or intraocular administration, the active principles of formula (I) above, or the possible salts, solvates or hydrates thereof, can be administered in unit administration forms, mixed with conventional pharmaceutical supports, to animals and human beings for the prophylaxis or treatment of the above disorders or conditions. The appropriate unit forms of administration comprise oral-route forms such as tablets, gel capsules, powders, granules and oral solutions or suspensions, sublingual, buccal, intratracheal and intranasal administration forms, subcutaneous, intramuscular or intravenous administration forms and rectal administration forms. For topical application, the compounds according to the invention can be used in creams, ointments, lotions or eyedrops.

In order to obtain the desired prophylactic or therapeutic effect, the dose of active principle can range between 0.02 mg and 1 mg per kg of body weight and per day.

Each unit dose can contain from 1 mg to 25 mg, preferably from 5 mg to 12 mg, of active ingredients in combination with a pharmaceutical support. This unit dose can be administered 1 to 5 times a day so as to administer a daily dosage of from 1 mg to 100 mg, preferably from 5 mg to 60 mg.

When a solid composition in the form of tablets is prepared, the main active ingredient is mixed with a pharmaceutical vehicle, such as gelatin, starch, lactose, magnesium stearate, talc, gum arabic or the like. The tablets can be coated with sucrose, with a cellulosic derivative, or with other suitable materials, or alternatively they can be treated such that they have a prolonged or delayed activity and such that they release a predetermined amount of active principle continuously.

A preparation in gel capsules is obtained by mixing the active ingredient with a diluent and pouring the mixture obtained into soft or hard gel capsules.

A preparation in the form of a syrup or elixir or for administration in the form of drops can contain the active ingredient together with a sweetener, preferably a calorie-free sweetener, methyl paraben and propyl paraben as antiseptic, as well as a flavour enhancer and a suitable dye.

The water-dispersible powders or granules can contain the active ingredient mixed with dispersants, wetting agents or suspending agents, such as polyvinylpyrrolidone, as well as with sweeteners or flavour enhancers.

For rectal administration, use is made of suppositories which are prepared with binders melting at rectal temperature, for example cocoa butter or polyethylene glycols.

For parenteral administration, use is made of aqueous suspensions, isotonic saline solutions or injectable sterile solutions which contain pharmacologically compatible dispersants and/or wetting agents, for example propylene glycol or butylene glycol.

The active principle can also be formulated in the form of microcapsules, optionally with one or more supports or additives, or alternatively with matrices such as a polymer or a cyclodextrin (patch, sustained-release forms).

The compositions of the present invention can contain, along with the products of formula (I) above or the pharmaceutically acceptable salts, solvates and hydrates thereof, other active principles which can be used in the treatment of the disorders or conditions indicated above.

Thus, a subject of the present invention is also pharmaceutical compositions containing several active principles in combination, one of which is a compound according to the invention.

The PREPARATIONS and EXAMPLES below illustrate the invention without, however, limiting it.

The melting points were measured according to the Micro-Kofler technique.

The nuclear magnetic resonance spectra were acquired in dimethyl sulphoxide except where otherwise mentioned, at 200 MHz, and the chemical shifts are expressed in ppm. The abbreviations used below are the following:

s=singlet; m=multiplet; d=doublet; t=triplet; q=quartet.

The phenyl group in the compounds (I) will be conventionally numbered hereinbelow as follows:

19

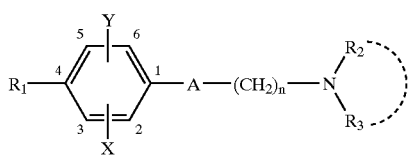

(I)

In the PREPARATIONS and EXAMPLES below, n is equal to 1.

PREPARATION 1

1-Bromo-4-(1,1-dimethoxyethyl)benzene, compound Vp (Vp): X=Y=H; Z=Br; P=$CH_3$

A mixture of 19.905 g of 1-(4-bromophenyl)ethanone, 101.4 ml of methanol, 0.22 g of para-toluenesulphonic acid hydrate and 19.9 ml of trimethyl orthoformate is stirred for 6 hours at room temperature. The solution is neutralized with a 1% solution of potassium hydroxide in methanol, and concentrated under reduced pressure. The oil obtained is taken up in petroleum ether, the precipitate is removed by filtration and the filtrate is evaporated under reduced pressure. Compound Vp is purified by distillation; yield=96%; b.p.=82° C. (at a pressure of 0.003 mbar).

PREPARATION 2

1-[4-(1-Hydroxy-3,3,5,5-tetramethylcyclohexyl)phenyl]ethanone, compound V'.1

(V'.1):

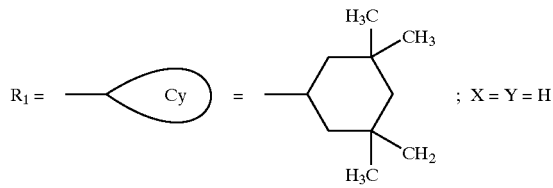

27.5 ml of a 1.6 M solution of n-butyllithium in hexane are added dropwise at −78° C. to a solution of 10 g of 1-bromo-4-(1,1-dimethoxyethyl)benzene (compound Vp) in 100 ml of tetrahydrofuran. The reaction mixture is stirred for 2 hours at this temperature. A solution of 6.92 ml of 3,3,5,5-tetramethylcyclohexanone in 20 ml of tetrahydrofuran is added over 20 minutes and the reaction mixture is stirred at −78° C. for 1 hour. After warming to room temperature, 140 ml of saturated aqueous ammonium chloride solution are added. The phases are separated after settling has taken place, the aqueous phase is extracted with diethyl ether, the organic phases are combined and dried over magnesium sulphate, and the solvents are evaporated off under reduced pressure. The oil obtained is purified by chromatography on a column of silica gel, eluting with a 95/5 (v/v) cyclohexane/ethyl acetate mixture; yield=88%; m.p.=135° C. The following compounds are prepared in the same way:

20

[4-(Hydroxy-3,3-dimethylcyclohexyl)phenyl]ethanone, compound V'.2

(V'.2):

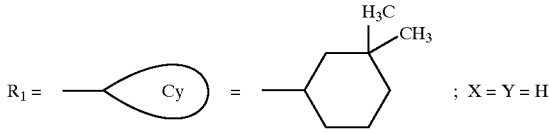

m.p.=99° C.

1-[4-(Hydroxyadamantan-2-yl)phenyl]ethanone, compound V'.3

(V'.3):

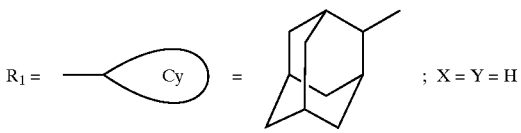

$^1$H NMR: 7.9 (d, 2H); 7.6 (d, 2H); 4.8 (s, 1H); 2.6–1.4 (m, 18H).

PREPARATION 3

1-[4-(3,3,5,5-Tetramethylcyclohexyl)phenyl]ethanone, compound V.1

(V.1):

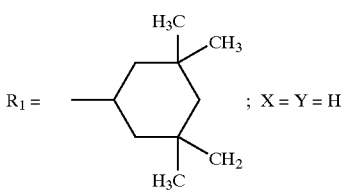

38.1 ml of chlorotrimethylsilane are added over 45 minutes to a solution of 40.45 g of 1-[4-(hydroxy-3,3,5,5-tetramethylcyclohexyl)phenyl]ethanone (compound V'.1) and 56.21 g of sodium iodide in 230 ml of anhydrous acetonitrile. During the addition, the temperature is maintained between 35° C. and 40° C. After stirring for 2 hours, 40 ml of acetonitrile and 39.4 ml of acetic acid are added. Next, 29.4 g of finely powdered zinc are added portionwise with stirring and at room temperature. The reaction mixture is refluxed with vigorous stirring for 4 hours. After cooling to room temperature, the reaction medium is filtered through Celite and then washed with saturated aqueous sodium bicarbonate solution. The organic phase is concentrated under reduced pressure and the oil obtained is purified by chromatography on a column of silica gel, eluting with a 95/5 (v/v) cyclohexane/ethyl acetate mixture; yield=68%; m.p.=54° C. The following compounds are obtained in the same way:

1-[4-(3,3-Dimethylcyclohexyl)phenyl]ethanone, compound V.2

(V.2):

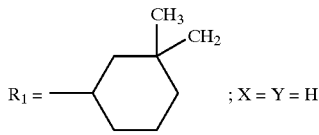

¹H NMR: 7.8 (d, 2H); 7.2 (d, 2H); 2.7 (m, 1H); 2.5 (s, 3H); 1.8–1.1 (m, 8H); 0.9 (s, 3H).

1-(4-Adamantan-2-ylphenyl)ethanone, compound V.3

(V.3):

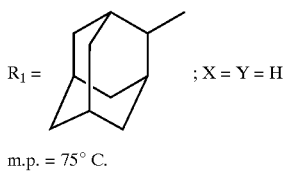

m.p. = 75° C.

m.p.=75° C.

PREPARATION 4

1-[3-Chloro-4-(3,3,5,5-tetramethylcyclohexyl) phenyl]ethanone, compound V.4

(V.4):

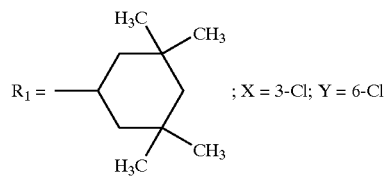

40.25 g of aluminium chloride are added at 0° C., under an inert atmosphere, to 350 ml of dichloromethane, followed by addition of 5 g of 1-[4-(3,3,5,5-tetramethylcyclohexyl) phenyl]ethanone (compound V.1) dissolved in dichloromethane. After stirring for 2 hours at 0° C., 17.1 ml of chlorine gas (d=1.565, measured in the liquid state at −78° C.) are bubbled through the reaction. After warming to room temperature, a water/ice mixture is added to the reaction mixture. The resulting mixture is extracted with dichloromethane, the phases are separated after settling has taken place, and the organic phase is dried over magnesium sulphate and concentrated under reduced pressure. The residue is purified on a column of silica gel, eluting with a 7/3 (v/v) cyclohexane/dichloromethane mixture; yield= 74%; m.p.=64° C.

The dichloro compounds are also isolated:

1-[3,5-Dichloro-4-(3,3,5,5-tetramethylcyclohexyl) phenyl]ethanone, compound V.5

(V.5):

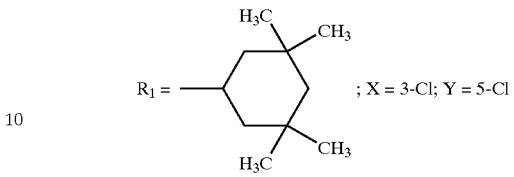

¹H NMR: 7.9 (s, 1H); 7.8 (s, 1H); 3.9 (m, 1H); 2.5 (s, 3H); 2.1 (m, 2H); 1.2 (m, 4H); 1.0 (s, 6H); 0.9 (s, 6H).

1-[3,6-Dichloro-4-(3,3,5,5-tetramethylcyclohexyl) phenyl]ethanone, compound V.6

(V.6):

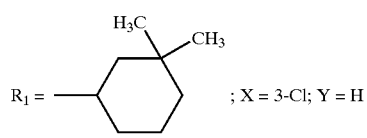

¹H NMR: 7.6 (s, 1H); 7.2 (s, 1H); 3.3 (m, 1H); 2.6 (s, 3H); 1.5 (m, 2H); 1.2 (m, 4H); 1.1 (s, 6H); 0.9 (s, 6H).

The following compounds are isolated according to the procedure described for compound V.4:

1-[3-Chloro-4-(3,3-dimethylcyclohexyl)phenyl] ethanone, compound V.7

(V.7):

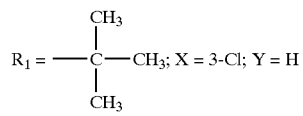

¹H NMR: 7.9 (s, 1H); 7.8 (d, 1H); 7.4 (d, 1H); 3.1 (m, 1H); 2.5 (s, 3H); 1.8–1.1 (m, 8H); 0.9 (s, 3H); 0.8 (s, 3H).

1-(3-Chloro-4-tert-butylphenyl)ethanone, compound V.8

(V.8):

$$R_1 = \overset{CH_3}{\underset{CH_3}{\overset{|}{C}}} CH_3; X = 3\text{-}Cl; Y = H$$

¹H NMR: 7.8 (s, 1H); 7.7 (d, 1H); 7.5 (d, 1H); 2.5 (s, 3H); 1.4 (s, 9H).

1-(3,5-Chloro-4-cyclohexylphenyl)ethanone, compound V.9

(V.9):

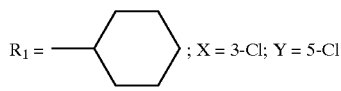 ; X = 3-Cl; Y = 5-Cl

PREPARATION 5

1-[(3-Chloro-4-hydroxy)phenyl]ethanone, compound VII.1

(VII.1): X=3-Cl; Y=H 167 g of aluminium trichloride are added, under an inert atmosphere, to 63.5 ml of 2-chloro-1-methoxybenzene in 500 ml of 1,2-dichloroethane, followed by dropwise addition of 167 g of acetyl chloride dissolved in 200 ml of 1,2-dichloroethane. The reaction mixture is heated at 45° C. for 48 hours. The reaction mixture is poured onto a water/ice mixture and extracted with dichloromethane, the solvents are evaporated off under reduced pressure and the residue obtained is purified by chromatography on a column of silica gel, eluting with a 90/10 (v/v) cyclohexane/ethyl acetate mixture. Compound VII.1 is recrystallized from cyclohexane; m.p.=107° C.

PREPARATION 6

1-Prop-2-ynylazepane, compound 4.1

(4.1):

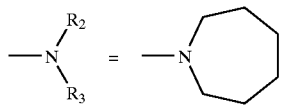

18.8 ml of a 3-bromopropyne solution at 80% in toluene are added dropwise to 20.8 ml of hexamethyleneamine and 27.9 g of potassium carbonate in 300 ml of acetonitrile. The reaction mixture is heated at 50° C. for 12 hours and 6 hours at 80° C. The reaction mixture is filtered, and the solvents are evaporated off under reduced pressure. Compound 4.1 is purified by distillation; b.p.=61° C. under a pressure of 26.7 Pa.

$^1$H NMR: 3.3 (s, 2H); 3.0 (s, 1H); 2.5 (m, 4H); 1.5 (m, 8H).

In the same way are prepared:

1-Prop-2-ynylazocane, compound 4.2

(4.2):

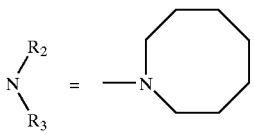

$^1$H NMR: 3.3 (s, 2H); 3.0 (s, 1H); 2.5 (m, 4H); 1.5 (m, 10H).

1-Prop-2-ynylpiperidine, compound 4.3

(4.3):

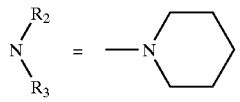

$^1$H NMR: 3.2 (s, 2H); 3.1 (s, 1H); 2.3 (m, 4H); 1.5 (m, 2H); 1.3 (m, 4H).

PREPARATION 7

4-Acetyl-2-chlorophenyl trifluoromethanesulphonate, compound Va.1

(Va.1): X=3-Cl; Y=H; Z=OTf 26.2 ml of triflic anhydride are added dropwise at 0° C. to 26.7 g of 1-[(3-chloro-4-hydroxy)phenyl]ethanone (compound VII.1) in 700 ml of pyridine. The reaction mixture is stirred at 0° C. for 36 hours, the solvents are evaporated off under reduced pressure and the residue is taken up in a 0.1 N solution of hydrochloric acid in dichloromethane. The phases are separated after settling has taken place, the organic phases are dried over magnesium sulphate and the solvents are evaporated off under reduced pressure. The residue obtained is purified by chromatography on a column of silica gel, eluting with a 95/5 (v/v) cyclohexane/ethyl acetate mixture.

$^1$H NMR: 8.2 (s, 1H); 8.0 (d, 1H); 7.8 (d, 1H).

The following compounds are prepared in the same way:

4-Acetyl-2,6-dichlorophenyl trifluoromethanesulphonate, compound Va.2

(Va.2): X=3-Cl; Y=6-Cl; Z=OTf $^1$H NMR: 8.2 (s, 2H); 2.6 (s, 3H).

4-Bromo-2-chlorophenyl trifluoromethanesulphonate, compound IIIa.1 starting with 4-bromo-2-chlorophenol (IIIa.1): X=3-Cl; Y=H $^1$H NMR: 8.1 (s, 1H); 7.7 (d, 1H); 7.6 (d, 1H).

4-Bromo-3-chlorophenyl trifluoromethanesulphonate, compound IIIa.2

(IIIa.2): X=2-Cl; Y=H $^1$H NMR: 8.0 (m, 2H); 7.5 (d, 1H).

4-Bromo-2-methylphenyl trifluoromethanesulphonate, compound IIIa.3

(IIIa.3): X=2-CH$_3$; Y=H $^1$H NMR: 7.7 (s, 1H); 7.6 (d, 1H); 7.3 (d, 1H); 2.3 (s, 3H).

4-Bromophenyl trifluoromethanesulphonate, compound IIIa.4

(IIIa.4): X=Y=H $^1$H NMR: 7.8 (d, 2H); 7.4 (d, 2H).

PREPARATION 8

4-[3-(1-Azepanyl)prop-1-ynyl]-2-chlorophenyl trifluoromethanesulphonate, compound Ia.1

(Ia.1):

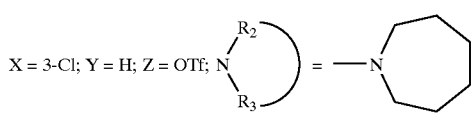

1.96 g of 1-prop-2-ynylazepane (compound 4.1) are added, under inert atmosphere, to 4 g of 4-bromo-2-chlorophenyl trifluoromethanesulphonate (compound IIIa.1), 0.062 g of copper iodide, 10 ml of pyridine and 20 ml of triethylamine, followed by 0.457 g of the catalyst dichlorobis(triphenylphosphine)palladium. The reaction mixture is heated at the reflux point for 2 hours, the solvents are evaporated off under reduced pressure, and the residue obtained is taken up in dichloromethane, washed in water and dried over magnesium sulphate. After evaporating off the solvents under reduced pressure, the residue obtained is purified by chromatography on a column of silica gel, eluting with an 80/20 cyclohexane/ethyl acetate mixture; m.p.=192° C.

$^1$H NMR: 7.8 (s, 1H); 7.5 (m, 2H); 3.6 (s, 2H); 2.6 (m, 4H); 1.5 (m, 8H).

The following compounds are prepared in the same way:

4-[3-(1-Azepanyl)prop-1-ynyl]-3-chlorophenyl trifluoromethanesulphonate, compound Ia.2

(Ia.2):

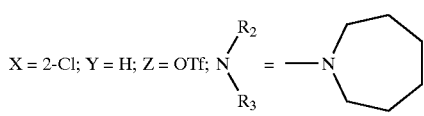

$^1$H NMR: 7.7 (d, 1H); 7.6 (s, 1H); 7.3 (d, 1H); 3.5 (s, 2H); 2.8 (m, 4H); 1.5 (m, 8H).

4-[3-(1-Azepanyl)prop-1-ynyl]-2-methylphenyl trifluoromethanesulphonate, compound Ia.3

(Ia.3):

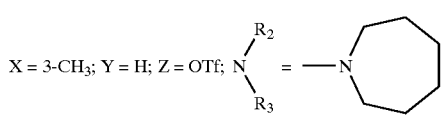

$^1$H NMR: 7.5 (s, 1H); 7.4 (m, 2H); 3.5 (s, 2H); 2.6 (m, 4H); 2.3 (s, 3H); 1.5 (m, 8H).

4-[3-(1-Azocanyl)prop-1-ynyl]-2-chlorophenyl trifluoromethanesulphonate, compound Ia.4

(Ia.4):

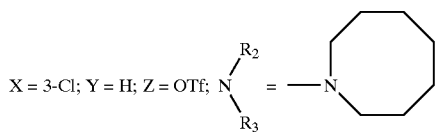

$^1$H NMR: 7.8 (s, 1H); 7.5 (m, 2H); 3.6 (s, 2H); 2.6 (m, 4H); 1.5 (m, 10H).

4-[3-(1-Piperidyl)prop-1-ynyl]2-chlorophenyl trifluoromethanesulphonate, compound Ia.5

(Ia.5):

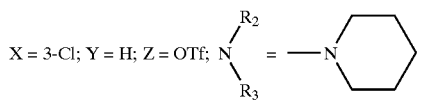

$^1$H NMR: 7.8 (s, 1H); 7.6 (m, 2H); 3.5 (s, 2H); 2.4 (m, 4H); 1.8–1.5 (m, 6H).

4-[3-(1-Azepanyl)prop-1-ynyl]phenyl trifluoromethanesulphonate, compound Ia.6

(Ia.6):

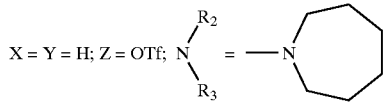

PREPARATION 9

1-[3-Chloro-4-(4-fluorophenyl)phenyl]ethanone, compound V.10

(V.10):

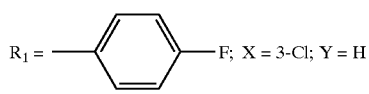

19.7 g of 4-acetyl-2-chlorophenyl trifluoromethanesulphonate (compound Va.1), 10 g of 4-fluorobenzeneboronic acid, 2 g of tetrakis(triphenylphosphine)palladium, 17.9 g of sodium carbonate in 84.5 ml of water, 591 ml of toluene, 200 ml of ethanol and 5.51 g of lithium chloride are stirred under an inert atmosphere at 60° C. for 8 hours. The reaction mixture is then stirred for 12 hours at room temperature. The resulting mixture is filtered and the solvents are evaporated from the filtrate under reduced pressure. The residue obtained is purified by chromatography on a column of silica gel, eluting with a 97/3 (v/v) cyclohexane/ethyl acetate mixture; yield=94%.

$^1$H NMR: 8.0 (1H, s); 7.9 (1H, d); 7.5 (3H, m); 7.3 (2H, m); 2.6 (3H, s).

The compounds V.11 to V.15 given in TABLE 1 below are prepared in the same way:

TABLE 1

(V)

R₁—⟨phenyl with Cl⟩—C(=O)—CH₃ with Y = H

| COMPOUND | R₁ | ¹H NMR |
|---|---|---|
| V.11 | 3-fluorophenyl | 8.1(s, 1H); 7.9(d, 1H); 7.5(m, 2H); 7.2(m, 3H); 2.6(s, 3H) |
| V.12 | 3,4-difluorophenyl | 8.0(s, 1H); 7.9(d, 1H); 7.6(m, 3H); 7.3(m, 1H); 2.6(s, 3H) |
| V.13 | 3,5-difluorophenyl | 8.0(s, 1H); 7.9(d, 1H); 7.6(d, 1H); 7.4–7.1(m, 3H); 2.6(s, 3H) |
| V.14 | 4-chlorophenyl | 8.0(s, 1H); 7.9(d, 1H); 7.5(m, 5H); 2.6(s, 3H) |
| V.15 | 4-methoxyphenyl (H₃CO-) | 8.0(s, 1H); 7.9(d, 1H); 7.5(d, 1H); 7.4(m, 2H); 7.0(m, 2H); 3.8(s, 3H); 2.6(s, 3H) |

1-(2,6-Dichlorobiphenyl-4-yl)ethanone, compound V.16

(V.16):

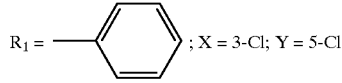 ; X = 3-Cl; Y = 5-Cl

¹H NMR: 8.0 (s, 2H); 7.4 (m, 3H); 7.2 (m, 2H); 2.6 (s, 3H).

1-(2,6-Dichloro-4'-fluorobiphenyl-4-yl)ethanone, compound V.17

(V.17):

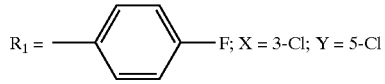 F; X = 3-Cl; Y = 5-Cl

¹H NMR: 8.0 (s, 2H); 7.3 (m, 4H) 2.6 (s, 3H).

PREPARATION 10

3-Chloro-3-[3-chloro-4-(3,3,5,5-tetramethylcyclohexyl)phenyl]propenal, compound IV.1

(IV.1)

R₁ = 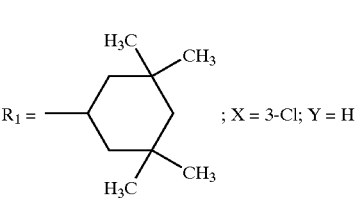 ; X = 3-Cl; Y = H 3.51 ml of oxalyl chloride are added dropwise at a temperature of between −5° C. and 2° C. to a solution of 3.72 ml of dimethylformamide and 20 ml of anhydrous dichloromethane and the reaction mixture is then stirred at room temperature for 30 minutes. 3.92 g of 1-[3-chloro-4-(3,3,5,5-tetramethylcyclohexyl)phenyl]ethanone (compound V.6) dissolved in 10 ml of dichloromethane are then added rapidly, after which the reaction mixture is stirred at room temperature for 12 hours. The reaction mixture is poured into a water/ice mixture and 20 ml of aqueous 2.84 M sodium ethoxide solution are then added. The resulting mixture is washed with 50 ml of sodium hydrogen carbonate solution and 50 ml of water, the phases are separated after settling has taken place, the organic phase is dried over magnesium sulphate and the solvents are evaporated off under reduced pressure. The oil obtained is purified by chromatography on a column of silica gel, eluting with a 97/3 (v/v) cyclohexane/ethyl acetate mixture.

¹H NMR: 10.2 (d, 1H); 7.7 (s, 1H); 7.5 (d, 1H); 7.3 (d, 1H); 6.6 (d, 1H); 3.4 (m, 1H); 1.5 (m, 2H); 1.3 (m, 4H); 1.1 (s, 6H); 0.9 (s, 6H).

Compounds IV.2 to IV.18 given in TABLES 2 and 3 below are prepared in the same way:

TABLE 2

(IV)

[structure: R₁—phenyl with X substituent, —C(Cl)=CH—CHO]

in which Y = H

| COMPOUND | R₁ | X | m.p.; ° C. or ¹H NMR |
|---|---|---|---|
| IV.2 | 3,3,5,5-tetramethylcyclohexyl | H | 10.1(d, 1H); 7.8(m, 2H); 7.4(m, 2H); 6.9(m, 1H); 2.9(m, 1H); 1.4–0.8(18H) |

TABLE 2-continued (IV)

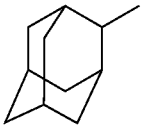

in which Y = H

| COMPOUND | R₁ | X | m.p.; ° C. or ¹H NMR |
|---|---|---|---|
| IV.3 | adamantyl | H | 146 |
| IV.4 | 4-F-phenyl | H | |
| IV.5 | 3-F-phenyl | H | |
| IV.6 | 1,3-dimethylcyclohexyl | Cl | 10.0(d, 1H); 7.8(s, 1H); 7.7 (d, 1H); 7.4(d, 1H); 7.0(d, 1H); 3.1(m, 1H); 1.8–1.1 (m, 8H); 1.0(s, 3H); 0.9(s, 3H) |
| IV.7 | tert-butyl | Cl | |
| IV.8 | 4-F-phenyl | Cl | 139 |
| IV.9 | 3-F-phenyl | Cl | |
| IV.10 | 3,4-diF-phenyl | Cl | |
| IV.11 | 3,5-diF-phenyl | Cl | |

TABLE 2-continued (IV)

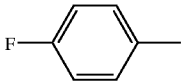

in which Y = H

| COMPOUND | R₁ | X | m.p.; ° C. or ¹H NMR |
|---|---|---|---|
| IV.12 | 4-Cl-phenyl | Cl | |
| IV.13 | 4-H₃CO-phenyl | Cl | 10.1(d, 1H); 8.0(s, 1H); 7.9 (d, 1H); 7.6–7.3(m, 3H); 7.1(m, 2H); 7.0(d, 1H); 3.8(s, 3H) |

TABLE 3

(IV)

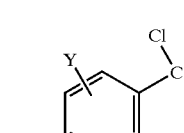

with X = Cl

| COMPOUND | R₁ | Y | m.p.; ° C. or ¹H NMR |
|---|---|---|---|
| IV.14 | 1,3,3,5-tetramethylcyclohexyl | 5-Cl | 10.1(d, 1H); 8.0(s, 1H); 7.9(s, 1H); 7.1(d, 1H); 3.9(m, 1H); 2.1(m, 2H); 1.3(m, 4H); 1.1(s, 6H); 0.9(s, 6H) |
| IV.15 | 1,3,3,5-tetramethylcyclohexyl | 6-Cl | 10.0(d, 1H); 7.8–7.4(m, 2H); 6.6(d, 1H); 3.2(m, 1H); 1.6–1.2(m, 6H); 1.0(s, 6H); 0.9(s, 6H) |
| IV.16 | cyclohexyl | 5-Cl | |
| IV.17 | phenyl | 5-Cl | 108 |

TABLE 3-continued (IV)

structure with X = Cl

| COMPOUND | R₁ | Y | m.p.; °C. or ¹H NMR |
|---|---|---|---|
| IV.18 | F-phenyl- | 5-Cl | |

PREPARATION 11

3-Chloro-4-(3,3,5,5-tetramethylcyclohexyl)phenylethyne, compound II.1

(II.1):

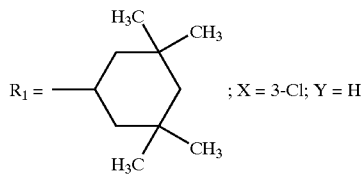

R₁ = 3,3,5,5-tetramethylcyclohexyl ; X = 3-Cl; Y = H 5.3 g of sodium hydroxide are dissolved in 150 ml of water under an inert atmosphere and with vigorous stirring. 80 ml of 1,4-dioxane are added and the mixture is refluxed. 15 g of 3-chloro-3-[3-chloro-4-(3,3,5,5-tetramethylcyclohexyl)phenyl]propenal (compound IV.1) dissolved in 130 ml of 1,4-dioxane are added rapidly, and the reaction mixture is maintained at reflux for 1 hour. After cooling to room temperature, the reaction mixture is poured into a large volume of dichloromethane. The phases are separated after settling has taken place, the organic phase is dried over magnesium sulphate and the solvents are evaporated off under reduced pressure. Purification is carried out by chromatography on a column of silica gel, eluting with cyclohexane; yield: 80%.

¹H NMR: 7.5 (1H, s); 7.3 (2H, m); 4.2 (1H, s); 3.2 (1H, m); 1.4 (2H, m); 1.2 (4H, m); 1.0 (6H, s); 0.9 (6H, s).

Compounds II.2 to II.16 given in TABLES 4 and 5 below are prepared in the same way:

TABLE 4

(II)

structure with Y = H

| COMPOUND | R₁ | Y | m.p.; °C. or ¹H NMR |
|---|---|---|---|
| II.2 | 3,3,5,5-tetramethylcyclohexyl | H | 7.3(d, 2H); 7.2(d, 2H); 4.1(s, 1H); 2.9(m, 1H); 1.5–1.1(m, 6H); 1.0(s, 6H); 0.9(s, 6H) |
| II.3 | adamantyl | H | |
| II.4 | 1,5-dimethylcyclohexyl | Cl | 7.4(s, 1H); 7.3(d, 1H); 7.2(d, 1H); 4.0(s, 1H); 3.0(m, 1H); 1.7–1.0(m, 8H); 0.9(s, 3H); 0.8(s, 3H) |
| II.5 | tert-butyl | Cl | 7.4(m, 3H); 4.2(s, 1H); 1.3(s, 9H) |
| II.6 | 4-F-phenyl | Cl | 7.6(s, 1H); 7.4(m, 6H); 4.3(s, 1H) |
| II.7 | 3-F-phenyl | Cl | 7.7(s, 1H); 7.5(m, 3H); 7.3(m, 3H); 4.3(s, 1H) |
| II.8 | 3,4-diF-phenyl | Cl | 7.7(s, 1H); 7.5(m, 4H); 7.3(m, 1H); 4.3(s, 1H) |
| II.9 | 3,5-diF-phenyl | Cl | |
| II.10 | 4-Cl-phenyl | Cl | 78 |
| II.11 | 4-MeO-phenyl | Cl | 7.6(s, 1H); 7.4(d, 1H); 7.3(m, 3H); 7.0(d, 2H); 4.3(s, 1H); 3.8(s, 3H) |

TABLE 5

(II)

structure: Y on top of benzene ring, R₁ on left, C≡CH on right, Cl on bottom with X = Cl

| COMPOUND | R₁ | Y | m.p.; ° C. or ¹H NMR |
|---|---|---|---|
| II.12 | 2,2,6,6-tetramethylcyclohexyl group (H₃C, CH₃ / H₃C, CH₃) | 5-Cl | 7.6(s, 1H); 7.5(s, 1H); 4.4(s, 1H); 3.9(m, 1H); 2.0(t, 2H); 1.2(m, 4H); 1.1(s, 6H); 0.9(s, 6H) |
| II.13 | 2,2,6,6-tetramethylcyclohexyl group (H₃C, CH₃ / H₃C, CH₃) | 6-Cl | 7.6(s, 1H); 7.4(s, 1H); 4.6(s, 1H); 3.2(m, 1H); 1.5–1.1(m, 6H); 1.0(s, 6H); 0.9(s, 6H) |
| III.14 | cyclohexyl | 5-Cl | |
| II.15 | phenyl | 5-Cl | 7.7(s, 2H); 7.4(m, 3H); 7.2(d, 2H); 4.5(s, 1H) |
| II.16 | 4-fluorophenyl | 5-Cl | 7.6(s, 2H); 7.3(d, 4H); 4.5(s, 1H) |

PREPARATION 12

3,5-Difluorobenzeneboronic acid, compound 2.1

91.5 ml of tert-butyllithium are added at −78° C. to 20 g of 1-bromo-3,5-difluorobenzene in 300 ml of diethyl ether. The reaction mixture is stirred for 1 hour at −78° C. and 14.2 ml of trimethyl borate are then added. The reaction mixture is stirred for 1 hour at −78° C. and then for 12 hours at room temperature. 200 ml of aqueous 1 N hydrochloric acid solution are added. The resulting mixture is extracted with diethyl ether, the organic phase is washed with saturated aqueous sodium hydrogen carbonate solution and dried over magnesium sulphate, and the solvents are evaporated off under reduced pressure. The residue is taken up in cyclohexane and the precipitate obtained is isolated by filtration.

¹H NMR: 7.4 (m, 3H); 7.2 (m, 2H).

PREPARATION 13

4-Bromo-3-chloroacetophenone, compound Va.3
(Va.3); X=3-Cl; Y=H; Z=Br

A solution of 100 g of 4-bromoacetophenone in 250 ml of dichloromethane is added dropwise at 0° C. to 133.34 g of aluminium chloride in 600 ml of dichloromethane. After stirring for 2 hours at 0° C., 28.3 ml of prefrozen (−75° C.) chlorine are bubbled through the medium at 0° C. The reaction mixture is stirred at room temperature for 12 hours and then hydrolysed. The phases are separated after settling has taken place, the aqueous phase is extracted with dichloromethane, the organic phases are dried over magnesium sulphate and the solvents are evaporated off under reduced pressure. The residue obtained is recrystallized from hexane; yield=57%; m.p.=80° C.

PREPARATION 14

3-Chloro-3-(4-bromo-3-chlorophenyl)propenal, compound IVa.1
(IVa.1): X=3-Cl; Y=H ; Z=Br 15.08 ml of oxalyl chloride are added at a temperature of between 3° C. and 6° C. with vigorous stirring to 16 ml of dimethylformamide in 200 ml of dichloromethane. After warming to room temperature, the mixture is stirred for 30 minutes, followed by addition of a solution of 13.4 g of 4-bromo-3-chloroacetophenone (compound Va.3) in 40 ml of dichloromethane. The reaction mixture is stirred for 12 hours at room temperature and then hydrolysed by addition of a solution of 18.9 g of sodium acetate in 50 ml of water. After stirring for 30 minutes at room temperature, the phases are separated after settling has taken place, the aqueous phase is extracted with dichloromethane, the organic phases are dried over magnesium sulphate and the solvents are evaporated off under reduced pressure. The residue obtained is recrystallized from cyclohexane; yield=87%; m.p=134° C.

PREPARATION 15

1-[3-(4-Bromo-3-chlorophenyl)prop-2-ynyl]azepane, compound Ia.7

(Ia.2):

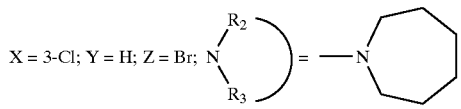

X = 3-Cl; Y = H; Z = Br; $N\begin{smallmatrix}R_2\\R_3\end{smallmatrix}$ = azepane N a) 1-Bromo-2-chloro-4-ethynylbenzene, compound IIa.1

6.9 g of sodium hydroxide are dissolved, under an inert atmosphere, in 220 ml of water, 100 ml of 1,4-dioxane are added and the reaction mixture is heated to 75° C. 16 g of 3-chloro-3-(4-bromo-3-chlorophenyl)propenal (compound IVa.1) dissolved in 400 ml of 1,4-dioxane are added and the reaction mixture is stirred for 30 minutes at 85° C. The reaction mixture is allowed to cool to room temperature and 1300 ml of dichloromethane are then added. The phases are separated after settling has taken place, the organic phase is washed with water and dried over magnesium sulphate and the solvents are evaporated off. The compound obtained is used directly in the next step.

b) 1-[3-(4-Bromo-3-chlorophenyl)prop-2-ynyl]azepane, compound Ia.7

2.53 ml of aqueous 36% formaldehyde solution are added to 2.46 ml of hexamethyleneimine in 40 ml of 1,2-dimethoxyethane. This solution is added to 4.28 g of the compound obtained above in the presence of 0.17 g of copper (II) chloride dihydrated in 120 ml of 1,2-dimethoxyethane. The reaction mixture is stirred for 1 hour at reflux, the solvents are evaporated off under reduced pressure and then the residue obtained is purified by chromatography on a column of silica gel, eluting with a cyclohexane/ethyl acetate mixture which varies from 90/10 to 80/20 (v/v); yield=82%.

$^1$H NMR: 7.7 (d, 1H); 7.6 (s, 1H); 7.2 (d, 1H); 3.5 (s, 2H); 2.6 (m, 4H); 1.5 (m, 8H).

PREPARATION 16

2-{2-Chloro-4-[3-(1-azepanyl)prop-1-ynyl]phenyl}adamantan-2-ol, compound I'.1

(I'.1):

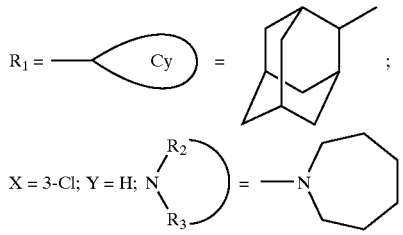

5.6 ml of a 15% solution of n-butyllithium in hexane are added, at −78° C., to 3.1 g of 1-[3-(4-bromo-3-chlorophenyl)prop-2-ynyl]azepane (compound Ia.7) in 50 ml of diethyl ether and stirring is maintained at −75° C. for 1 hour. Still at −78° C., 1.38 g of 2-amandatanone in 25 ml of diethyl ether are added, and the reaction mixture is then stirred for 1 hour at −78° C.

The reaction mixture is allowed to return to room temperature, and then a water/ice mixture is added. The phases are separated after settling has taken place, they are extracted with diethyl ether, the organic phases are dried over sodium sulphate and the solvents are evaporated off under reduced pressure. The residue obtained is purified by chromatography on a column of silica gel, eluting with an 85/15 (v/v) cyclohexane/ethyl acetate mixture; yield=73%; m.p.=95° C.

PREPARATION 17

4,4-Dimethylcyclohexanone, compound 3.1 a) 4,4-Dimethylcyclohex-2-enone 1 ml of concentrated sulphuric acid is added at room temperature to 81 ml of but-3-en-2-one and 88 ml of 2-methylpropionaldehyde in 450 ml of benzene, and then the reaction mixture is refluxed for 13 hours to remove the water by azeotropic entrainment. After cooling to room temperature, the reaction mixture is washed with a saturated aqueous sodium bicarbonate solution and then with water. The organic phase is dried over magnesium sulphate and the solvents are evaporated off under reduced pressure. After distillation, 31.1 g of the expected compound are isolated; b.p.=78° C. (at a pressure of 22 mbar).

b) 31.1 g of 4,4-dimethylcyclohex-2-enone in 100 ml of pentane are hydrogenated in an autoclave at a pressure of 5 bar in the presence of 1.6 g of 5% palladium on charcoal. The reaction mixture is filtered and the solvents are evaporated off under reduced pressure.

PREPARATION 18

2-Chloro-4-(4,4-dimethylcyclohexyl)phenol, compound IX.1 a) 2-Chloro-4-(1-hydroxy-4,4-dimethylcyclohexyl)phenol 100 ml of a 1.6 M solution of butyllithium in hexane are added at −78° C. to 15.1 g of 4-bromo-2-chlorophenol in 150 ml of tetrahydrofuran, and the reaction mixture is stirred for 1 hour at −78° C. 10.1 g of 4,4-dimethylcyclohexanone (compound 3.1) are added and the reaction mixture is stirred at −78° C. for a further 30 minutes and then at room temperature for 12 hours. The reaction mixture is hydrolysed with 1N hydrochloric acid solution and extracted with ethyl acetate. The organic phase is dried over magnesium sulphate and the solvents are evaporated off under reduced pressure. The solid obtained is purified by chromatography on a column of silica gel, eluting with a cyclohexane/ethyl acetate mixture which varies from 98/2 to 90/10 (v/v). 11.8 g of solid are obtained.

$^1$H NMR: 7.4 (s, 1H); 7.2 (d, 2H); 6.9 (d, 2H); 4.5 (s, 1H); 1.9–1.1 (m, 8H); 0.9 (s, 6H).

b) 50 ml of an aqueous 57% hydriodic acid solution are added to 11.8 g of 2-chloro-4-(1-hydroxy-4,4-dimethylcyclohexyl)phenol in 200 ml of acetic acid. The reaction mixture is heated at reflux for 3 hours and the solvents are evaporated off under reduced pressure. Aqueous 40% sodium hydroxide solution, aqueous sodium carbonate solution and then aqueous sodium hydrogen sulphate solution are added and the resulting mixture is extracted with diethyl ether. The organic phase is dried over magnesium sulphate and the solvents are evaporated off under reduced pressure. The compound obtained is purified by chromatography on a column of silica gel, eluting with a 95/5 (v/v) cyclohexane/ethyl acetate mixture.

$^1$H NMR: 9.8 (s, 1H); 7.1 (s, 1H); 7 (d, 1H); 6.9 (d, 1H); 1.9 (m, 1H); 1.6–1.2 (m, 8H); 0.9 (s, 6H).

PREPARATION 19

2-Chloro-4-(4,4-dimethylcyclohexyl)phenyl trifluoromethanesulphonate, compound III.1

8.2 ml of triflic anhydride are added at 5° C. to 9.7 g of 2-chloro-4-(4,4-dimethylcyclohexyl)phenol (compound IX.1) in 60 ml of pyridine, the reaction mixture is left to stand for 30 minutes at 0° C., and then the reaction mixture is stirred at room temperature for 12 hours. The reaction mixture is hydrolysed and then extracted with dichloromethane. The organic phase is dried over magnesium sulphate and the solvents are evaporated off under reduced pressure. The residue obtained is taken up in toluene, and then the solvents are evaporated off under reduced pressure. The residue obtained is purified by chromatography on a column of silica gel, eluting with a cyclohexane/ethyl acetate mixture which varies from 100/0 to 99/1 (v/v). 15 g of the compound are obtained.

$^1$H NMR: 7.7 (s, 1H); 7.5 (d, 1H); 7.4 (d, 1H); 2.5 (m, 1H); 1.6–1.2 (m, 8H); 0.92 (s, 3H); 0.86 (s, 3H).

EXAMPLE 1

1-{3-[3-Chloro-4-(3,3,5,5-tetramethylcyclohexyl)phenyl]prop-2-ynyl}azepane hydrochloride (I):

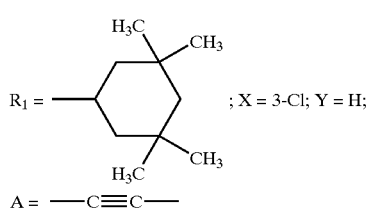

-continued

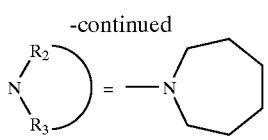

0.08 g of copper (II) chloride dihydrate is added, under an inert atmosphere, to 2.57 g of 3-chloro-4-(3,3,5,5-tetramethylcyclohexyl)phenylethyne (compound II.1) in 20 ml of 1,2-dimethoxyethane (DME). A solution of 1.19 ml of formaldehyde and 1.162 ml of hexamethyleneimine in 10 ml of DME is then added rapidly. The reaction mixture is heated at reflux for one hour. After cooling to room temperature, the solvents are evaporated off under reduced pressure. The residue is taken up in diethyl ether and gaseous hydrochloric acid is bubbled through with fast stirring. The precipitate obtained is isolated by filtration. This precipitate is dried under reduced pressure and then recrystallized from toluene; yield=75%; m.p.=187° C. (HCl).

The EXAMPLES 2 to 16 given in TABLES 6 and 7 below are prepared in the same way:

TABLE 6

(I)

with Y = H

| EXAMPLE | $R_1$ | X | m.p.; ° C. or $^1$H NMR |
|---|---|---|---|
| 2 | 3,3,5,5-tetramethylcyclohexyl | H | 200 HCl |
| 3 | adamantyl | H | 158 HCl-0.2 H$_2$O |
| 4 | 3,3,5-trimethylcyclohexyl | Cl | 176 HCl |
| 5 | tert-butyl | Cl | 190 HCl-0.3 H$_2$O |
| 6 | 4-fluorophenyl | Cl | 210 HCl |

TABLE 6-continued (I)

with Y = H

| EXAMPLE | $R_1$ | X | m.p.; ° C. or $^1$H NMR |
|---|---|---|---|
| 7 | 3-fluorophenyl | Cl | 186 HCl-0.3 H$_2$O |
| 8 | 3,4-difluorophenyl | Cl | 7.6–7.2(m, 6H); 3.6(s, 2H); 2.6(m, 4H); 1.8–1.4(m, 8H) |
| 9 | 3,5-difluorophenyl | Cl | 196 HCl |
| 10 | 4-chlorophenyl | Cl | 223 HCl |
| 11 | 4-methoxyphenyl | Cl | 220 HCl |

TABLE 7

(I)

with X = Cl

| EXAMPLE | $R_1$ | Y | m.p.; ° C. or $^1$H NMR (salt) |
|---|---|---|---|
| 12 | 3,3,5,5-tetramethylcyclohexyl | 5-Cl | 7.5(s, 1H); 7.4(s, 1H); 3.8(m, 1H) 3.5(s, 2H); 2.6(m, 4H); 2.0(t, 2H) 1.5(m, 8H); 1.2(m, 4H); 1.0(s, 6H) 0.8(s, 6H) |

TABLE 7-continued (I)

R₁—[phenyl with Y, Cl]—C≡C—CH₂—N[azepane]

with X = Cl

| EX-AM-PLE | R₁ | Y | m.p.; °C. or ¹H NMR (salt) |
|---|---|---|---|
| 13 | [3,3,5,5-tetramethylcyclohexyl with H₃C groups] | 6-Cl | 7.5(s, 1H); 7.4(s, 1H); 3.6(s, 2H) 3.3(m, 1H); 2.7(m, 4H); 2.4(m, 2H); 1.5(m, 8H); 1.3(m, 4H); 1.0(s, 6H); 0.9(s, 6H) |
| 14 | cyclohexyl | 5-Cl | |
| 15 | phenyl | 5-Cl | 230 HCl |
| 16 | 4-fluorophenyl | 5-Cl | 184 HCl |

EXAMPLE 17

1-[3-(4-Adamantan-2-yl-3-chlorophenyl)prop-2-ynyl]azepane hydrochloride (I):

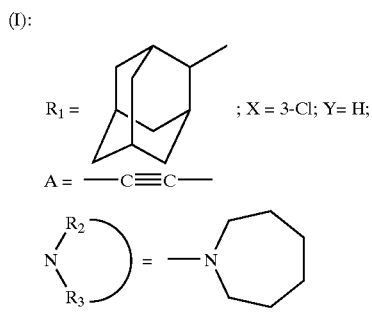

R₁ = [adamantan-2-yl] ; X = 3-Cl; Y= H;

A = —C≡C—

N(R₂)(R₃) = —N[azepane]

3.46 g of sodium iodide are added, under an inert atmosphere, to 3.68 g of 2-{2-chloro-4-[3-(1-azepanyl)prop-1-ynyl]phenyl}adamantan-2-ol (compound I'.1) in 20 ml of acetonitrile and 10 ml of dichloromethane, followed by 2.35 ml of chlorotrimethylsilane. The reaction mixture is stirred for 2 hours at 30° C., and then 1.06 ml of acetic acid are added, followed by 10 ml of acetonitrile and then 1.81 g of powdered zinc. The reaction mixture is heated at 80° C. for 3 hours, allowed to cool to room temperature, filtered and washed with diethyl ether. The organic phases are dried over sodium sulphate, and then the solvents are evaporated off under reduced pressure. The residue obtained is purified by chromatography on a column of silica gel, eluting with an 87.5/12.5 (v/v) cyclohexane/ethyl acetate mixture; m.p.= 218° C. (HCl).

EXAMPLE 18

1-[3-(2-Chloro-3',5'-difluorobiphenyl-4-yl)prop-2-ynyl]azepane hydrochloride (I):

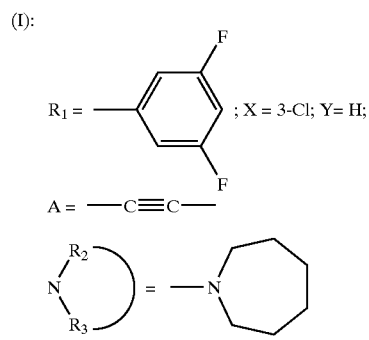

R₁ = [3,5-difluorophenyl] ; X = 3-Cl; Y= H;

A = —C≡C—

N(R₂)(R₃) = —N[azepane]

9.5 g of 4-[3-(1-azepanyl)prop-1-ynyl]-2-chlorophenyl trifluoromethanesulphonate (compound Ia.1), 5 g of 3,5-difluorobenzeneboronic acid (compound 2.1), 31 ml of 2 M aqueous sodium carbonate solution, 2.1 g of lithium chloride, 300 ml of toluene, 100 ml of ethanol and 0.7 g of tetrakis(triphenylphosphine)palladium are stirred for 12 hours at 80° C. under an inert atmosphere. The solvents are evaporated off under reduced pressure and the residue obtained is purified by chromatography on a column of silica gel, eluting with a 99/1 (v/v) toluene/ethanol mixture. The compound obtained is taken up in diethyl ether and hydrochloric acid is bubbled through. The precipitate obtained is filtered off and recrystallized from toluene; m.p.=196° C. (HCl).

The compounds of EXAMPLES 19 to 32 given below are prepared in the same way:

TABLE 8

(I)

R₁—[phenyl with Y, X]—C≡C—CH₂—N[azepane]

| EXAMPLE | R₁ | X | Y | m.p.; °C. (salt, hydrate) |
|---|---|---|---|---|
| 19 | 3,5-difluorophenyl | 2-Cl | H | 205 HCl |
| 20 | 3-(trifluoromethyl)phenyl (F₃C) | 3-Cl | H | 172 HCl |
| 21 | 4-(trifluoromethyl)phenyl (F₃C) | 3-Cl | H | 198 HCl |

TABLE 8-continued (I)

| EXAMPLE | R₁ | X | Y | m.p.; °C. (salt, hydrate) |
|---|---|---|---|---|
| 22 | 3,5-difluorophenyl | 3-CH₃ | H | 175 HCl 0.8 H₂O |
| 23 | 3-chlorophenyl | 3-Cl | H | (a) |
| 24 | 2-fluorophenyl | 3-Cl | H | (b) |
| 25 | 2,4-difluorophenyl | 3-Cl | H | 184 HCl |
| 26 | 3,5-dichlorophenyl | 3-Cl | H | (c) |
| 27 | 2-fluoro-4-fluorophenyl | 3-Cl | H | (d) |
| 28 | 3-methoxyphenyl | 3-Cl | H | 175 HCl 0.4 H₂O |
| 29 | 3,5-difluorophenyl | H | H | 167 HCl |
| 30 | 4,4-dimethylcyclohexyl | 2-Cl | H | 205 HCl |

(a) ¹H NMR: 7.7–7.3(m, 7H); 3.6(s, 2H); 2.7(m, 4H); 1.6(m, 8H)
(b) ¹H NMR: 7.6–6.8(m, 7H); 3.5(d, 2H); 2.6(m, 4H); 1.5(m, 8H)
(c) ¹H NMR: 7.8(s, 1H); 7.7(s, 1H); 7.6–7.5(m, 4H); 4.3(s, 2H); 3.4–3.3 (m, 4H); 1.9(m, 4H); 1.6(m, 4H)
(d) ¹H NMR: 7.8(s, 1H); 7.6–7.1(m, 5H); 4.3(s, 2H); 3.4(m, 2H); 3.3(m, 2H); 1.8(m, 4H); 1.6(m, 4H)

EXAMPLE 31

1-{3-[4-(3,5-Difluorophenyl)-3-chlorophenyl]prop-2-ynyl}azocane hydrochloride (I): R₁ = 3,5-difluorophenyl; X = 3-Cl; Y = H;

A = —C≡C—;

$\begin{matrix} R_2 \\ N \\ R_3 \end{matrix}$ = azocan-1-yl m.p. = 182° C. (HCl; 0.1 H₂O)

EXAMPLE 32

{3-[4-(3,5-Difluorophenyl)-3-chlorophenyl]prop-2-ynyl}piperidine hydrochloride (I): R₁ = 3,5-difluorophenyl; X = 3-Cl; Y = H;

A = —C≡C—;

$\begin{matrix} R_2 \\ N \\ R_3 \end{matrix}$ = piperidin-1-yl m.p. = 220° C. (HCl)

EXAMPLE 33

{3-[4-(4,4-Dimethylcyclohexyl)-3-chlorophenyl] prop-2-ynyl}azepane hydrochloride (I):

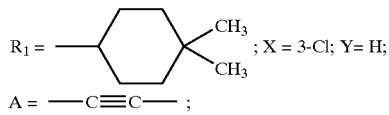 ; X = 3-Cl; Y= H;

A = —C≡C— ;

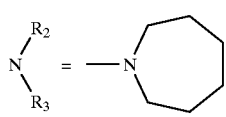

0.76 g of dichlorobis(triphenylphosphine)palladium are added, under an inert atmosphere, to 3.6 g of 1-prop-2-ynylazepane (compound 4.1), 8 g of [4-(4,4-dimethylcyclohexyl)-3-chlorophenyl] trifluoromethanesulphonate (compound III.1), 0.103 g of copper iodide, 1.83 g of lithium chloride in 200 ml of triethylamine and 100 ml of pyridine. The reaction mixture is heated at reflux for 12 hours. The solvents are evaporated off under reduced pressure and the residue obtained is purified by chromatography on a column of silica gel, eluting with a 95/5 (v/v) cyclohexane/ethyl acetate mixture. The residue obtained is taken up in diethyl ether and the hydrochloride is formed by bubbling hydrochloric acid through. After filtration, the residue obtained is recrystallized from toluene.

EXAMPLE 34

1-{(Z)-3-[3-Chloro-4-(3,3,5,5-tetramethylcyclohexyl)phenyl]propen-2-yl}azepane hydrochloride (I):

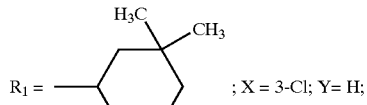 ; X = 3-Cl; Y= H;

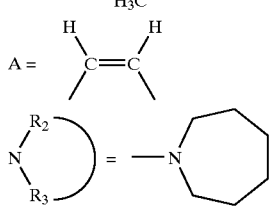

2.28 g of the compound of EXAMPLE 1 in 40 ml of petroleum ether are hydrogenated, under an inert atmosphere and at atmospheric pressure, in the presence of 2.3 ml of cyclohexene and 0.23 g of palladium on calcium carbonate poisoned with 3.5% lead (Lindlar catalyst). The reaction mixture is filtered through Celite, the oily residue obtained is taken up in diethyl ether and hydrochloric acid is bubbled through. The precipitate is filtered off and dried under reduced pressure; m.p.=190° C. (HCl). The compounds of EXAMPLES 35 to 64 below are prepared in the same way:

TABLE 9

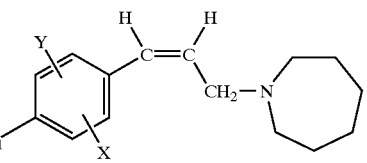 (I)

| EXAMPLE | R₁ | X | Y | m.p.; ° C. (salt, hydrate) |
|---|---|---|---|---|
| 35 | 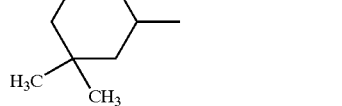 | H | H | 120 HCl |
| 36 | 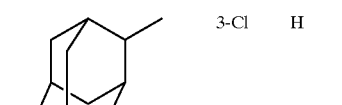 | H | H | 186 HCl |
| 37 | 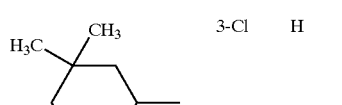 | 3-Cl | H | 162 HCl |
| 38 | 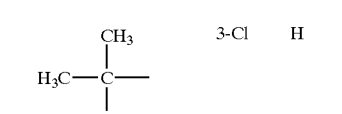 | 3-Cl | H | 155 HCl |
| 39 | 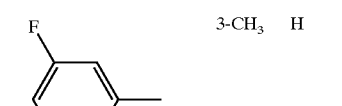 | 3-Cl | H | 158 HCl |
| 40 |  | 3-CH₃ | H | 115 HCl 0.6 H₂O |
| 41 |  | 3-Cl | H | 164 HCl 0.3 H₂O |
| 42 | 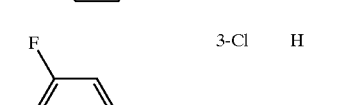 | 3-Cl | H | 179 HCl |
| 43 | F <br>(3-fluorophenyl) | 3-Cl | H | 152 HCl |

TABLE 9-continued (I)

[Structure: Y and R1 substituted phenyl ring connected via CH=CH-CH2 to N-azepane, with X also on ring]

| EXAMPLE | R₁ | X | Y | m.p.; °C. (salt, hydrate) |
|---|---|---|---|---|
| 44 | 3,4-difluorophenyl | 3-Cl | H | 138 HCl |
| 45 | 3,5-difluorophenyl | 3-Cl | H | 139 HCl |
| 46 | 4-chlorophenyl | 3-Cl | H | 146 HCl |
| 47 | 4-methoxyphenyl | 3-Cl | H | 142 HCl |
| 48 | 3,5-difluorophenyl | 2-Cl | H | 161 HCl 0.2 H₂O |
| 49 | 3-trifluoromethylphenyl | 3-Cl | H | 150 HCl |
| 50 | 4-trifluoromethylphenyl | 3-Cl | H | 141 HCl 0.2 H₂O |
| 51 | 3-chlorophenyl | 3-Cl | H | 147 HCl |
| 52 | 2,4-difluorophenyl | 3-Cl | H | 128 HCl |
| 53 | 3,5-dichlorophenyl | 3-Cl | H | 220 HCl |
| 54 | 2,4-difluorophenyl | 3-Cl | H | 158 HCl |
| 55 | 3-methoxyphenyl | 3-Cl | H | 132 HCl |
| 56 | 3,5-difluorophenyl | H | H | 157 HCl |
| 57 | 4,4-dimethylcyclohexyl | 3-Cl | H | 179 HCl 0.2 H₂O |
| 58 | 3,3,5,5-tetramethylcyclohexyl | 3-Cl | 5-Cl | 191 HCl·0.2 H₂O |
| 59 | 3,3,5,5-tetramethylcyclohexyl | 3-Cl | 6-Cl | 181 HCl |
| 60 | cyclohexyl | 3-Cl | 5-Cl | |
| 61 | phenyl | 3-Cl | 5-Cl | 228 HCl |

TABLE 9-continued

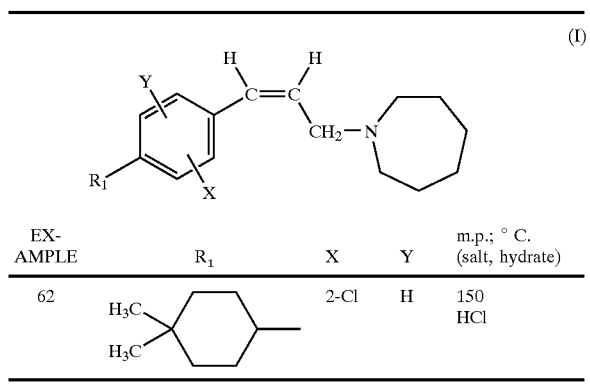

| EXAMPLE | $R_1$ | X | Y | m.p.; °C. (salt, hydrate) |
|---|---|---|---|---|
| 62 | 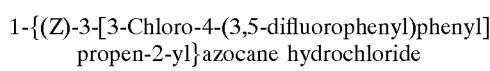 | 2-Cl | H | 150 HCl |

EXAMPLE 63

1-{(Z)-3-[3-Chloro-4-(3,5-difluorophenyl)phenyl]propen-2-yl}azocane hydrochloride (I):

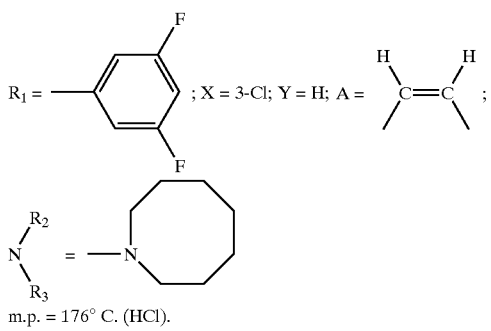

m.p. = 176° C. (HCl).

EXAMPLE 64

1-{(Z)-3-[3-Chloro-4-(3,5-difluorophenyl)phenyl]propen-2-yl}piperidine hydrochloride (I):

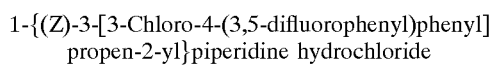

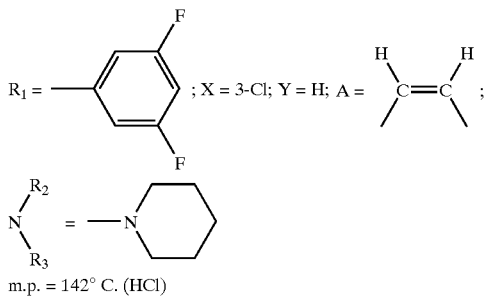

m.p. = 142° C. (HCl)

EXAMPLE 65

1-{(E)-3-[3-Chloro-4-(3,3,5,5-tetramethylcyclohexyl)phenyl]propen-2-yl}azepane hydrochloride (I):

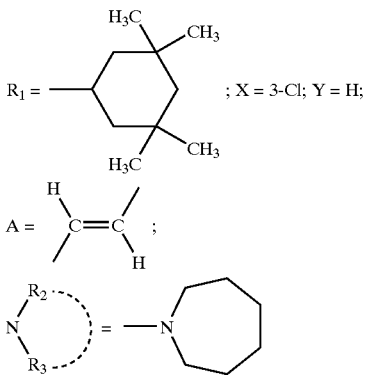

19.5 ml of a 1 M solution of diisobutylaluminium hydride (DIBALH) in toluene are added dropwise, under an inert atmosphere, to a solution of 3 g of the compound of EXAMPLE 1 in 25 ml of toluene. The reaction mixture is stirred at 40° C. for 1 hour and is then poured into a water/ice mixture. The resulting mixture is extracted with dichloromethane, the phases are separated after settling has taken place, the organic phase is dried over magnesium sulphate and the solvents are evaporated off under reduced pressure. The residue is taken up in diethyl ether and hydrogen chloride is bubbled through. The precipitate obtained is filtered off and dried; yield=74%; m.p.=205° C. (HCl).

The compounds of EXAMPLES 66 to 69 given in TABLE 10 below are prepared in the same way:

TABLE 10

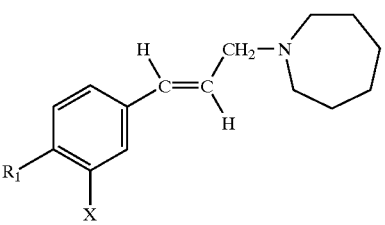

with Y = H

| EXAMPLE | $R_1$ | X | m.p.; °C. (salt, hydrate) |
|---|---|---|---|
| 66 |  | H | 182 HCl 0.2 $H_2O$ |

TABLE 10-continued (I) Structure: R1-phenyl(X)-CH=CH-CH2-N(azepane), with Y = H

| EXAMPLE | R1 | X | m.p.; °C. (salt, hydrate) |
|---|---|---|---|
| 67 | adamantyl | H | 226 HCl |
| 68 | 4-F-phenyl | Cl | 239 HCl |
| 69 | 3,5-diF-phenyl | Cl | 202 HCl 0.2 H₂O |

EXAMPLE 70

1-{3-[3-Chloro-4-(3,3,5,5-tetramethylcyclohexyl)phenyl]propyl}azepane hydrochloride (I):

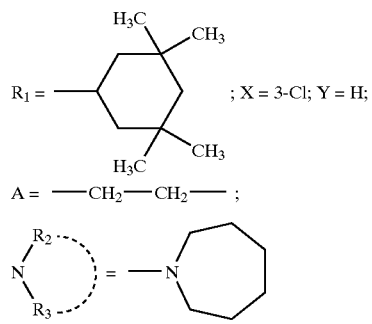

R1 = 3,3,5,5-tetramethylcyclohexyl; X = 3-Cl; Y = H;

A = —CH₂—CH₂—;

N(R2)(R3) = azepane 3.6 g of the compound of EXAMPLE 1 are hydrogenated in the presence of 0.36 g of 10% palladium on charcoal and 50 ml of ethanol. The reaction mixture is filtered, and the filtrate is evaporated off under reduced pressure. The oily residue obtained is taken up in diethyl ether and hydrochloric acid is bubbled through. The precipitate obtained is filtered off and dried; yield=59%; m.p.=215° C. (HCl).

The compounds of EXAMPLES 71 to 85 given in TABLE 11 below are prepared in the same way:

TABLE 11

(I) Structure: R1-phenyl(X,Y)-CH2-CH2-CH2-N(azepane)

| EXAMPLE | R1 | X | Y | m.p.; °C. (salt) |
|---|---|---|---|---|
| 71 | 1,1,3,3-tetramethylcyclohexyl | H | H | 186 HCl 0.3 H₂O |
| 72 | adamantyl | H | H | 198 HCl |
| 73 | 4-F-phenyl | H | H | 180 HCl |
| 74 | 3-F-phenyl | H | H | 187 HCl·0.3 H₂O |
| 75 | 1,1-dimethyl-cyclohexyl (with 3-CH₃) | 3-Cl | H | 177 HCl |
| 76 | tert-butyl | 3-Cl | H | 178 HCl·0.6 H₂O |
| 77 | 4-F-phenyl | 3-Cl | H | 218 HCl·0.2 H₂O |
| 78 | 4-Cl-phenyl | 3-Cl | H | 201 HCl |
| 79 | 4-H₃CO-phenyl | 3-Cl | H | <50 CF₃COOH, 0.7 H₂O |
| 80 | 3,5-diF-phenyl | 3-CH₃ | H | 165 HCl |

TABLE 11-continued

(I)

| EXAMPLE | R₁ | X | Y | m.p.; °C. (salt) |
|---|---|---|---|---|
| 81 | | 3-Cl | H | 176 HCl 0.9 H₂O |
| 82 | | 3-Cl | H | 195 HCl |
| 83 | | 3-Cl | H | 177 HCl |
| 84 | | 3-Cl | 5-Cl | 210 CF₃COOH 0.4 H₂O |
| 85 | | H | H | 196 HCl 0.1 H₂O |

What is claimed is:

1. A compound of formula:

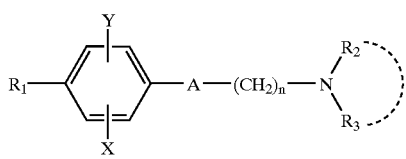
(I)

in which:

A represents a group chosen from the following:

n is equal to 1 or 2;

X represents a hydrogen, chlorine or fluorine atom or a methyl or methoxy group;

Y represents a hydrogen atom or a chlorine or fluorine atom;

$R_1$ represents a cyclohexyl group monosubstituted, disubstituted, trisubstituted or tetrasubstituted with a methyl group; a phenyl group monosubstituted or disubstituted with a fluorine or chlorine atom or with a ($C_1$–$C_3$)alkoxy or trifluoromethyl group; a cycloheptyl, tert-butyl, dicyclopropylmethyl, bicyclo[3.2.1]octanyl, 4-tetrahydropymanyl, 4-tetrahydrothiopyranyl or 1- or 2-adamantyl group; or $R_1$ represents a phenyl group, it being understood that, in this case, X or Y is other than hydrogen; or $R_1$ represents a cyclohexyl group, it being understood that, in this case, X and Y are other than hydrogen;

$R_2$ and $R_3$ form, with the nitrogen atom to which they are bonded, a 7-membered amine ring;

and the addition salts of these compounds with pharmaceutically acceptable acids, as well as the solvates and hydrates thereof.

2. A compound according to claim 1 in which:

A represents a group chosen from the following:

—C≡C—; —CH=CH—, —CH₂—CH₂— n is equal to 1;

X represents a hydrogen or chlorine atom or a methyl group;

Y represents a hydrogen or chlorine atom;

$R_1$ represents a cyclohexyl group monosubstituted, disubstituted, trisubstituted or tetrasubstituted with a methyl group; a phenyl group monosubstituted or disubstituted with a fluorine or chlorine atom or with a methoxy or trifluoromethyl group; a tert-butyl or 1- or 2-adamantyl group; or $R_1$ represents a phenyl group, it being understood that, in this case, X and Y are other than hydrogen; or else $R_1$ represents a cyclohexyl group, it being understood that, in this case, X and Y are other than hydrogen;

$R_2$ and $R_3$ form, with the nitrogen atom to which they are bonded, a 7-membered amine ring;

and the addition salts of these compounds with pharmaceutically acceptable acids, as well as the solvates and hydrates thereof.

3. A compound according to claim 2 of formula:

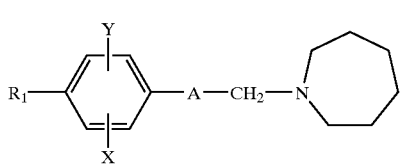
(I.1)

in which:

A represents a group chosen from the following:

X represents a hydrogen or chlorine atom;

Y represents a hydrogen atom or a chlorine atom;

$R_1$ represents a cyclohexyl group monosubstituted, disubstituted, trisubstituted or tetrasubstituted with a methyl group; a phenyl group mono- or disubstituted with a fluorine or chlorine atom or a methoxy group; a tert-butyl or 1- or 2-adamantyl group; or $R_1$ represents a cyclohexyl or phenyl group, it being understood that, in this case, X and Y are other than hydrogen;

and the addition salts of these compounds with pharmaceutically acceptable acids, as well as the solvates and hydrates thereof.

4. A compound according to claim 3 in which A represents the —CH=CH— group, in particular of (Z) configuration.

5. A compound according to claim 4 in which X represents a chlorine atom and Y represents a hydrogen atom.

6. A compound according to claim 5 in which $R_1$ represents a phenyl group monosubstituted or disubstituted with a fluorine or chlorine atom or a methoxy group, and the addition salts of these compounds with pharmaceutically acceptable acids, as well as the solvates and hydrates thereof.

7. A compound:
1-[(Z)-3-(2-chloro-3'-fluorobiphenyl-4-yl)propen-2-yl]azepane;
1-[(Z)-3-(2-chloro-3'-5'-difluorobiphenyl-4-yl)propen-2-yl]azepane;
1-[(Z)-3-(2-chloro-3'-methoxybiphenyl-4-yl)propen-2-yl]azepane;

according to claim 1, as well as the salts with pharmaceutically acceptable acids, solvates and hydrates thereof.

8. A compound 1-[(Z)-3-(2-chloro-3'-methoxybiphenyl-4-yl)propen-2-yl]azepane according to claim 1, as well as the salts with pharmaceutically acceptable acids, solvates and hydrates thereof.

9. A method for preparing a compound of formula:

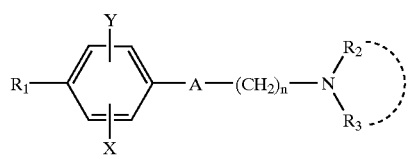

according to claim 1 in which A represents a —C≡C— group, wherein:
a) either, if n=1, a Mannich reaction is carried out between the phenylacetylene derivative of formula:

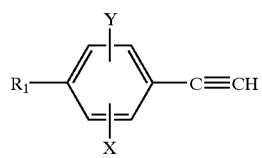

in which $R_1$, X and Y are as defined for (I), the formaldehyde and the amine (1) $HNR_2R_3$, $R_2$ and $R_3$ being as defined for (I);

b) or a Suzuki coupling is carried out between the compound of formula:

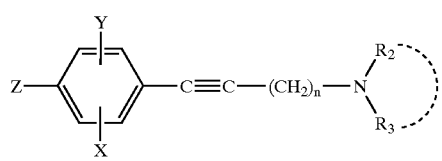

in which X, Y, n, $R_2$ and $R_3$ are as defined for (I) and Z represents a bromine, an iodine or a trifluoromethanesulphonate (OTf) group, and a boron derivative (2) of formula $R_1$—$B(OR)_2$ in which $R_1$ is as defined for (I) and R represents a hydrogen atom, an alkyl or aryl group in the presence of a base and a metal catalyst;

c) or, when $R_1$ represents a cyclohexyl group monosubstituted, disubstituted, trisubstituted or tetra-substituted with a methyl group; a cycloheptyl, 4-tetrahydropyranyl, 4-tetrahydrothiopyranyl or adamantyl group, a coupling is carried out between the compound (Ia) in which Z represents an iodine or bromine atom and the ketone (3) corresponding to $R_1$ represented by

in the presence of a base, to give the intermediate compound of formula:

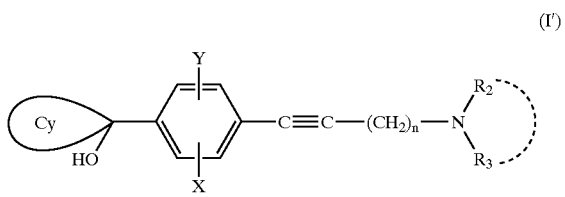

in which X, Y, n, $R_2$ and $R_3$ are as defined for (I); said compound (I') then being reduced under selective conditions;

d) or a coupling reaction is carried out between the amine of formula:

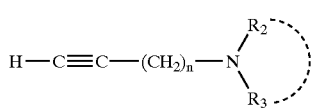

in which n, $R_2$ and $R_3$ are as defined for (I), and the compound of formula:

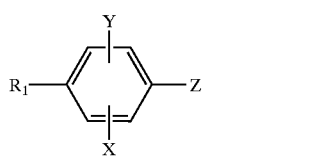

in which $R_1$, X and Y are as defined for (I) and Z represents a bromine or iodine atom or a trifluoromethylsulphonate (triflate or OTf) group.

10. A method for preparing a compound of formula:

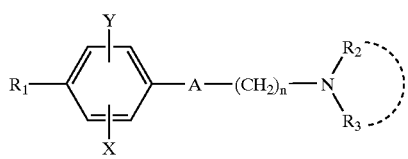

according to claim 1 in which A represents a —CH=CH— group wherein a hydrogenation with nascent hydrogen or in the presence of cyclohexene is carried out on compound (I) in which A represents an acetylene group —C≡C—, in order to prepare the ethylenic compound (I) in the form of a mixture of the Z and E isomers, or this hydrogenation is carried out in the presence of a metal catalyst on a support in order to prepare the ethylenic compound (I) in Z form, or alternatively compound (I) in which A represents an acetylene group —C≡C— is reacted with a metal hydride in order to prepare the ethylenic compound (I) in E form.

11. A method for preparing a compound of formula:

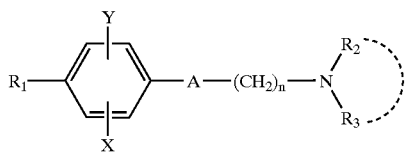 (I)

according to claim 1 in which A represents a —CH$_2$—CH$_2$— group wherein a hydrogenation is carried out on compound (I) in which A represents a —CH=CH— or —C≡C— group.

12. A pharmaceutical composition containing as active principle a compound according to claim 1.

13. A method for treating the positive and negative symptoms of schizophrenia which comprises administering to a patient in need of such treatment and effective amount of a compound according to claim 1.

14. A pharmaceutical composition containing as active principle a compound according to claim 2.

15. A pharmaceutical composition containing as active principle a compound according to claim 3.

16. A pharmaceutical composition containing as active principle a compound according to claim 4.

17. A pharmaceutical composition containing as active principle a compound according to claim 5.

18. A pharmaceutical composition containing as active principle a compound according to claim 6.

19. A pharmaceutical composition containing as active principle a compound according to claim 7.

20. A pharmaceutical composition containing as active principle a compound according to claim 8.

21. A method for treating the positive and negative symptoms of schizophrenia which comprises administering to a patient in need of such treatment an effective amount of a compound according to claim 2.

22. A method for treating the positive and negative symptoms of schizophrenia which comprises administering to a patient in need of such treatment an effective amount of a compound according to claim 3.

23. A method for treating the positive and negative symptoms of schizophrenia which comprises administering to a patient in need of such treatment an effective amount of a compound according to claim 4.

24. A method for treating the positive and negative symptoms of schizophrenia which comprises administering to a patient in need of such treatment an effective amount of a compound according to claim 5.

25. A method for treating the positive and negative symptoms of schizophrenia which comprises administering to a patient in need of such treatment an effective amount of a compound according to claim 6.

26. A method for treating the positive and negative symptoms of schizophrenia which comprises administering to a patient in need of such treatment an effective amount of a compound according to claim 7.

27. A method for treating the positive and negative symptoms of schizophrenia which comprises administering to a patient in need of such treatment an effective amount of a compound according to claim 8.

* * * * *